(12) United States Patent
Horie et al.

(10) Patent No.: US 10,813,873 B2
(45) Date of Patent: Oct. 27, 2020

(54) HAIR COSMETIC

(71) Applicant: KAO CORPORATION, Tokyo (JP)

(72) Inventors: Yu Horie, Koto-ku (JP); Kenji Hozumi, Wakayama (JP); Takashi Mizooku, Wakayama (JP); Hiroto Tanamachi, Yachiyo (JP)

(73) Assignee: KAO CORPORATION, Tokyo (JP)

( * ) Notice: Subject to any disclaimer, the term of this patent is extended or adjusted under 35 U.S.C. 154(b) by 873 days.

(21) Appl. No.: 15/116,409

(22) PCT Filed: Jun. 4, 2014

(86) PCT No.: PCT/JP2014/064882
§ 371 (c)(1),
(2) Date: Aug. 3, 2016

(87) PCT Pub. No.: WO2015/122029
PCT Pub. Date: Aug. 20, 2015

(65) Prior Publication Data
US 2017/0007526 A1    Jan. 12, 2017

(30) Foreign Application Priority Data

Feb. 17, 2014  (JP) ................. 2014-027161
Feb. 17, 2014  (JP) ................. 2014-027163

(51) Int. Cl.
| A61Q 5/08 | (2006.01) |
| A61Q 5/10 | (2006.01) |
| A61K 8/81 | (2006.01) |
| A61Q 5/02 | (2006.01) |
| A61Q 5/12 | (2006.01) |
| A61Q 5/06 | (2006.01) |

(52) U.S. Cl.
CPC ............ *A61K 8/8147* (2013.01); *A61K 8/817* (2013.01); *A61Q 5/02* (2013.01); *A61Q 5/06* (2013.01); *A61Q 5/08* (2013.01); *A61Q 5/10* (2013.01); *A61Q 5/12* (2013.01); *A61K 2800/5424* (2013.01); *A61K 2800/5426* (2013.01)

(58) Field of Classification Search
None
See application file for complete search history.

(56) References Cited

U.S. PATENT DOCUMENTS

| 4,240,450 A | 12/1980 | Grollier et al. |
| 4,657,690 A | 4/1987 | Grollier et al. |
| 4,668,508 A | 5/1987 | Grollier et al. |
| 6,423,305 B1 | 7/2002 | Cauwet-Martin et al. |
| 2003/0152542 A1 | 8/2003 | Decoster et al. |
| 2006/0293197 A1 | 12/2006 | Uehara et al. |
| 2006/0293213 A1 | 12/2006 | Uehara et al. |
| 2007/0108418 A1 | 5/2007 | Soane et al. |
| 2009/0211036 A1 | 8/2009 | Ascione |
| 2012/0058062 A1* | 3/2012 | Carson ............ A61K 8/06 424/59 |
| 2016/0120783 A1 | 5/2016 | Horie et al. |

FOREIGN PATENT DOCUMENTS

| JP | 53-139734 A | 12/1978 |
| JP | 59-172413 A | 9/1984 |
| JP | 10-95714 A | 4/1998 |
| JP | 2000-510491 A | 8/2000 |
| JP | 2000-264821 A | 9/2000 |
| JP | 2002-193772 A | 7/2002 |
| JP | 2004-91401 A | 3/2004 |
| JP | 2004-269400 A | 9/2004 |
| JP | 2004-323423 A | 11/2004 |
| JP | 2005-36014 A | 2/2005 |
| JP | 2005-330193 A | 12/2005 |
| JP | 2006-282674 A | 10/2006 |
| JP | 2006-347970 A | 12/2006 |
| JP | 2007-291016 A | 11/2007 |
| JP | 2007-297368 A | 11/2007 |
| JP | 2008-266254 A | 11/2008 |
| JP | 2008-290953 A | 12/2008 |

(Continued)

OTHER PUBLICATIONS

International Search Report dated Sep. 9, 2014 in PCT/JP2014/064882 filed Jun. 4, 2014.

(Continued)

*Primary Examiner* — Jyothsna A Venkat
(74) *Attorney, Agent, or Firm* — Oblon, McClelland, Maier & Neustadt, L.L.P.

(57) ABSTRACT

A hair cosmetic containing Components (A) and (B):

(A) a cationic polymer having a charge density of 5.0 to 7.0 meq/g; and (B) an anionic polymer comprising 80% by mass or more and 100% by mass or less of a constitutional unit represented by Formula (1) and having a weight-average molecular weight of 4,000 or more and 80,000 or less,

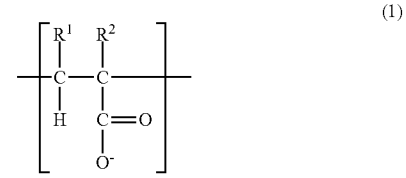

(1)

where $R^1$ represents a hydrogen atom or a carboxy group; and $R^2$ represents a hydrogen atom or a methyl group.

11 Claims, No Drawings

(56) References Cited

FOREIGN PATENT DOCUMENTS

| JP | 2008-543949 A | 12/2008 |
|---|---|---|
| JP | 2008-546806 A | 12/2008 |
| JP | 2009-504661 A | 2/2009 |
| JP | 2012-106960 A | 6/2012 |
| JP | 2012-136464 A | 7/2012 |
| JP | 2013-56846 A | 3/2013 |
| JP | 2015-151373 A | 8/2015 |
| JP | 2015-151374 A | 8/2015 |
| WO | 2007/002564 A1 | 1/2007 |
| WO | 2007/002565 A1 | 1/2007 |
| WO | 2007/021730 A2 | 2/2007 |
| WO | WO 2009/111455 A1 | 9/2009 |

OTHER PUBLICATIONS

Extended European Search Report dated Aug. 9, 2017 in Patent Application No. 14882544.1.

* cited by examiner

HAIR COSMETIC

CROSS REFERENCE TO RELATED APPLICATION

This application is a 371 of PCT/JP2014/064882, filed on Jun. 4, 2014, and claims priority to Japanese Patent Application No. 2014-027161, filed on Feb. 17, 2014 and to Japanese Patent Application No. 2014-027163, filed on Feb. 17, 2014.

FIELD OF THE INVENTION

The present invention relates to hair cosmetic.

BACKGROUND OF THE INVENTION

Hair is damaged by weathering, such as hair color treatment, permanent wave treatment, heating with a hair dryer, exposure to sunlight, and daily hair washing. As a result, the good feeling and beautiful appearance inherently possessed by healthy hair are impaired. To tackle this problem, methods are known to apply a hair cosmetic to the hair such that a conditioning component remains on the surface or surface layer of the hair (for example, see Patent Literatures 1 to 3).

However, since these conventional conditioning components do not sufficiently retain the effects, some techniques for retaining the effect of the component remaining on the hair, even after repeated hair washing certain times, have been proposed. For example, there are known a hair treating agent containing a specific polymer (for example, see Patent Literatures 4 and 5), a hair treating composition containing a copolymer prepared by solution polymerization of an ethylenically unsaturated monomer component (for example, see Patent Literature 6), and a hair hold formulation employing a combination of specific polymers (for example, see Patent Literature 7).

In addition, among hair bleach or dye compositions, in particular, two-part oxidative hair bleach or dye compositions damage hair and induce hair entanglement or deterioration in feel during hair washing with water or a shampoo. Furthermore, this hair entanglement causes loss of hair gloss and difficulty in styling after finishing. In addition, dyed hair is further damaged by physical irritation, e.g., by heat of a blow dryer, hair iron, or another material and daily hair care behavior such as brushing. Consequently, the feel due to hair entanglement during hair washing with water or a shampoo is further deteriorated, and the hair gloss and manageability after finishing are further reduced.

Accordingly, in order to enhance the effects, such as good feel in wetting and after drying, the durability of the feel, and the color retention, a technique for increasing the adsorption amount of silicones by using a specific cationic polymer together with an amino-modified silicone and a highly polymerized silicone has been proposed (Patent Literature 8).

Meanwhile, a hair bleach or dye composition containing both an amphoteric or cationic polymer and an anionic polymer and thereby enhancing the hair gloss and softness and further providing natural dyeing and sufficient fastness has been proposed (Patent Literature 9).

A conditioning composition containing a cationic surfactant and an anionic or amphoteric polymer and optionally a cationic polymer has been also proposed (Patent Literature 10). This literature mentions polyacrylic acid as an example of the anionic polymer (paragraph [0051]) and a dimethyl diallyl ammonium chloride homopolymer and an acrylamide/dimethyl diallyl ammonium chloride copolymer as preferred examples of the cationic polymer (paragraph [0079]).

(Patent Literature 1) JP-A-2004-323423
(Patent Literature 2) JP-A-2008-543949
(Patent Literature 3) JP-A-2006-282674
(Patent Literature 4) JP-A-2005-36014
(Patent Literature 5) JP-A-H10-95714
(Patent Literature 6) JP-A-2012-136464
(Patent Literature 7) JP-A-2009-504661
(Patent Literature 8) JP-A-2008-290953
(Patent Literature 9) JP-A-2002-193772
(Patent Literature 10) JP-A-2008-546806

SUMMARY OF THE INVENTION

The present inventors have found that a hair cosmetic containing a specific cationic polymer and a specific anionic polymer can solve the above-described problems all at once.

The present invention provides a hair cosmetic comprising the following Components (A) and (B):

(A) a cationic polymer having a charge density of 5.0 meq/g or more and 7.0 meq/g or less; and
(B) an anionic polymer comprising 80% by mass or more and 100% by mass or less of a constitutional unit represented by Formula (1) and having a weight-average molecular weight of 4,000 or more and 80,000 or less.

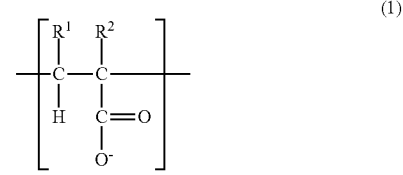

where $R^1$ represents a hydrogen atom or a carboxy group; and $R^2$ represents a hydrogen atom or a methyl group.

DETAILED DESCRIPTION OF THE INVENTION

The techniques described in Patent Literatures 4 to 7 are all insufficient in the effect of improving the appearance and feel of damaged hair to be like those of healthy hair. In particular, they do not consider the effect of improving the finger combability of wet hair. In addition, although some two-part hair bleach or dye compositions contain conditioning components, most of these additives are washed away by hair washing or rinsing after the treatment. Thus, the amounts of these additives remaining on the hair are low, and the effects thereof are insufficiently exhibited. Furthermore, also in the technique of Patent Literature 8, the durability of the effect is restricted and is insufficient. Patent Literatures 9 and 10 do not describe the durability of the effects at all.

The present invention relates to a hair cosmetic that can improve the feel and appearance of damaged hair to be like those of healthy hair, in particular, can enhance the finger combability of wet hair and the manageability of dried hair, and can retain these effects without deterioration by repeating hair washing.

In the specification, when the hair cosmetic is a hair bleach or dye composition, the term "first part" refers to a composition containing an alkaline agent; the term "second part" refers to a composition containing hydrogen peroxide; and the term "third part" refers to a composition containing an active component other than the alkaline agent and hydrogen peroxide. Regarding each component, the content "in a hair bleach or dye composition" refers to the content "in the hair bleach or dye composition" when the composition is of a one-part system, the content "in the mixture of the first part and the second part" when the composition is of a two-part system, and the content "in the mixture of the first to third parts" when the composition is of a three-part system.

<Component (A): Cationic Polymer Having a Charge Density of 5.0 meq/g or More and 7.0 meq/g or Less>

The hair cosmetic of the present invention contains a cationic polymer having a charge density of 5.0 meq/g or more and 7.0 meq/g or less. Herein, the charge density of a cationic polymer is defined as (the number of moles of the cationic groups in 1 g of the polymer)×1,000 (meq/g).

The charge density of Component (A) is preferably 5.2 meq/g or more, more preferably 5.5 meq/g or more, more preferably 5.8 meq/g or more, and even more preferably 6.0 meq/g or more, from the viewpoint of the durability of the good finger combability of wet hair and the durability of the manageability of dried hair, and is preferably 6.5 meq/g or less, from the viewpoint of providing good feel.

Examples of Component (A) include polymers comprising a diallyl quaternary ammonium salt as a constitutional unit and quaternized polyvinylimidazolium derivatives.

The polymers comprising a diallyl quaternary ammonium salt as a constitutional unit preferably have skeletons represented by Formula (2) or (3):

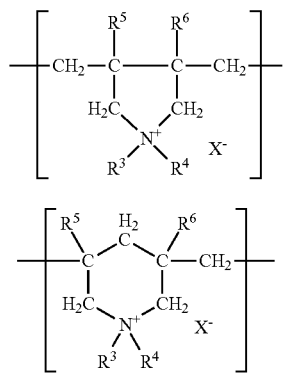

where $R^3$ and $R^4$ may be the same or different and each represent a hydrogen atom, an alkyl group, an aryl group (such as phenyl group), a hydroxy alkyl group, an amido alkyl group, a cyanoalkyl group, an alkoxyalkyl group, or a carboalkoxyalkyl group having 1 to 18 carbon atoms; $R^5$ and $R^6$ may be the same or different and each represent a hydrogen atom, an alkyl group having 1 to 3 carbon atoms, or a phenyl group; and $X^-$ represents an anion (such as a chloride ion, a bromide ion, an iodide ion, a sulfate anion, a sulfonate anion, a methylsulfate anion, phosphate anion, or a nitrate anion).

Each molecule of the polymer of a diallyl quaternary ammonium salt comprises the constitutional unit represented by Formula (2) or (3) in an amount of preferably from 65% to 100 mol %, more preferably from 75% to 100 mol %, more preferably from 90% to 100 mol %, and even more preferably 95% to 100 mol %, from the viewpoint of the durability of good combability of wet hair by fingers or comb and the durability of the manageability and gloss feel of dried hair.

Examples of the polymers comprising a diallyl quaternary ammonium salt as a constitutional unit include those represented by Formula (4) or (5):

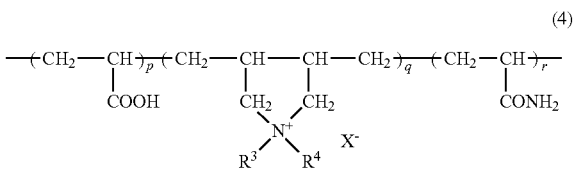

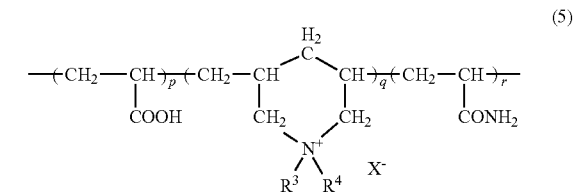

where $R^3$, $R^4$, and $X^-$ are synonymous with those mentioned above; and p, q, and r each represent a molar ratio, and p+q+r=100.

p is preferably from 0 to 50, more preferably from 0 to 25, more preferably from 0 to 10, and even more preferably from 0 to 5. q is preferably from 50 to 100, more preferably from 65 to 100, more preferably from 75 to 100, more preferably from 90 to 100, and even more preferably from 95 to 100. r is preferably from 0 to 50, more preferably from 0 to 25, more preferably from 0 to 10, and even more preferably from 0 to 5.

Among these components, preferred are homopolymers of diallyl quaternary ammonium salts and copolymers of diallyl quaternary ammonium salts and acrylic acid. Examples of the homopolymers of diallyl quaternary ammonium salts include Merquat 100 (manufactured by Lubrizol Advanced Materials, Inc., charge density: 6.2 meq/g, weight-average molecular weight: 150,000). Examples of the copolymers of diallyl quaternary ammonium salts and acrylic acid include Merquat 295 (manufactured by Lubrizol Advanced Materials, Inc., charge density: 6.0 meq/g, weight-average molecular weight: 190,000) and Merquat 280 (manufactured by Lubrizol Advanced Materials, Inc., charge density: 5.0 meq/g, weight-average molecular weight: 450,000).

The quaternized polyvinylimidazolium derivative is preferably represented by Formula (6):

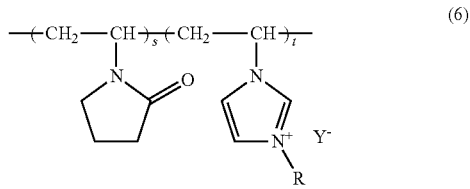

where R represents a hydrogen atom or an alkyl group having 1 to 3 carbon atoms; $Y^-$ represents an anion, such as a chloride ion, a bromide ion, an iodide ion, a sulfate anion, a sulfonate anion, an alkylsulfate anion having 1 to 4 carbon atoms, a phosphate anion, or a nitrate anion; and s and t each represent a molar ratio, and s+t=100.

The molar ratio t of the monomer having cationic properties is preferably 73 or more, more preferably 90 or more, and even more preferably 93 or more and is preferably 99 or less, from the viewpoint of the durability of good combability of wet hair by fingers or comb and the durability of the manageability and gloss feel of dried hair.

Examples of such quaternized polyvinylimidazolium derivatives include copolymers of vinylpyrrolidone and methylvinylimidazolium chloride (Luviquat Excellence: manufactured by BASF SE, charge density: 6.1 meq/g, weight-average molecular weight: 40,000).

Component (A) preferably has a weight-average molecular weight of 10,000 or more, more preferably 50,000 or more, and even more preferably 100,000 or more, from the viewpoint of the durability of good combability of wet hair by fingers or comb and the durability of the manageability and gloss feel of dried hair, and preferably 3,000,000 or less, more preferably 1,000,000 or less, and more preferably 800,000 or less, from the viewpoint of providing good feel.

The weight-average molecular weight can be measured by, for example, gel permeation chromatography (GPC) under the following conditions:

Mobile phase: 50 mM LiBr, 1% $CH_3COOH$/ethanol: water=3:7,

Column: TSK gel α-M (two columns connected in series), and

Reference material: polyethylene glycol.

Among these examples of Component (A), preferred are homopolymers of diallyl quaternary ammonium salts and copolymers of diallyl quaternary ammonium salts and acrylic acid.

When the hair cosmetic is a two-part or three-part hair bleach or dye composition, Component (A) may be contained in any of the first part, second part, and third part.

The content of Component (A) in the hair cosmetic is preferably 0.01% by mass or more, more preferably 0.1% by mass or more, more preferably 0.5% by mass or more, and even more preferably 0.75% by mass or more and is preferably 20% by mass or less, more preferably 10% by mass or less, more preferably 5% by mass or less, more preferably 3% by mass or less, more preferably 2.5% by mass or less, and even more preferably 2% by mass or less, from the viewpoint of the durability of good combability of wet hair by fingers or comb and the durability of the manageability and gloss feel of dried hair.

<Component (B): Anionic Polymer Having a Weight-Average Molecular Weight of 4,000 or More and 80,000 or Less>

The hair cosmetic of the present invention contains an anionic polymer comprising 80% by mass or more and 100% by mass or less of a constitutional unit represented by Formula (1) and having a weight-average molecular weight of 4,000 or more and 80,000 or less.

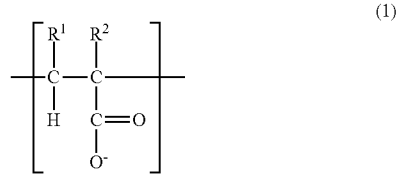

(1)

where $R^1$ represents a hydrogen atom or a carboxy group; and $R^2$ represents a hydrogen atom or a methyl group.

Component (B) comprises the constitutional unit represented by Formula (1) in an amount of preferably 85% by mass or more, more preferably 90% by mass or more, more preferably 95% by mass or more, and even more preferably 100% by mass.

Component (B) preferably has a weight-average molecular weight of 5,000 or more, more preferably 6,000 or more, more preferably 7,000 or more, and even more preferably 10,000 or more, from the viewpoint of the durability of good combability of wet hair by fingers or comb and the durability of the manageability and gloss feel of dried hair, and preferably 50,000 or less, more preferably 30,000 or less, more preferably 20,000 or less, and even more preferably 18,000 or less, from the viewpoint of providing good feel.

The weight-average molecular weight can be measured by, for example, gel permeation chromatography (GPC) under the following conditions:

Mobile phase: phosphate buffer containing 0.1 M sodium chloride, and

Column: TSK gel G4000PWXL+G3000PWXL+G2500PWXL (three columns connected in series).

Examples of Component (B) include Jurymer series AC-10NPD (weight-average molecular weight: 6,000), AC-10P (weight-average molecular weight: 5,000), AC-103 (weight-average molecular weight: 6,000), and AC-10S (weight-average molecular weight: 5,000) manufactured by Toagosei Co., Ltd.; Aron series T-50 (weight-average molecular weight: 6,000), A-20UK (weight-average molecular weight: 6,000), A-20UN (weight-average molecular weight: 20,000), and A-10SL (weight-average molecular weight: 6,000) manufactured by Toagosei Co., Ltd.; and Aqualic series DL-365 (weight-average molecular weight: 5,000), YS-100 (weight-average molecular weight: 5,500), and HL-415 (weight-average molecular weight: 10,000) manufactured by Nippon Shokubai Co., Ltd.

When the hair cosmetic is a hair bleach or dye composition, Component (B) is preferably contained in the first part of a two-part system and is preferably contained in the first part or the third part, more preferably in the third part, of a three-part system, from the viewpoint of stability.

The content of Component (B) in the hair cosmetic is preferably 0.01% by mass or more, more preferably 0.1% by mass or more, more preferably 0.3% by mass or more, and even more preferably 0.5% by mass or more and preferably 20% by mass or less, more preferably 10% by mass or less, more preferably 5% by mass or less, more preferably 3% by mass or less, more preferably 2% by mass or less, more preferably 1.5% by mass or less, and even more preferably 1.25% by mass or less, from the viewpoint of the durability of good combability of wet hair by fingers or comb and the durability of the manageability and gloss feel of dried hair.

The mass ratio of Component (A) to Component (B), (A)/(B), in the hair cosmetic of the present invention is preferably 0.1 or more, more preferably 0.5 or more, more preferably 0.75 or more, more preferably 1 or more, and even more preferably 1.2 or more and preferably 30 or less, more preferably 15 or less, more preferably 10 or less, more preferably 5 or less, and even more preferably 3 or less, from the viewpoint of the durability of good combability of wet hair by fingers or comb and the durability of the manageability and gloss feel of dried hair.

When the hair cosmetic is a two-part or three-part hair bleach or dye composition, Component (A) and Component (B) are preferably contained in different parts, from the viewpoint of stability. In the two-part system, the first part preferably contains Component (B), and the second part preferably contains Component (A). In the three-part system, the first part or the third part preferably contains Component (B), and the second part preferably contains Component (A).

[Surfactant]

The hair cosmetic of the present invention may contain a surfactant. When the hair cosmetic is a two-part or three-part hair bleach or dye composition, the surfactant may be contained in any of the first part, the second part, and the third part. The surfactant may be any of anionic surfactants, nonionic surfactants, cationic surfactants, and amphoteric surfactants.

Examples of the anionic surfactant include: sulfuric acid, ester-based anionic surfactants, such as alkyl sulfates and alkyl ether sulfates; carboxylic acid-based anionic surfactants, such as N-acylamino acid salts, N-acyl-N-alkylamino acid salts, amide N-acylamino acid salts, ether carboxylates, fatty acid salts, alkyl succinates, and alkenyl succinates; sulfonic acid-based anionic surfactants, such as sulfosuccinate-type, isethionate-type, taurine-type, alkylbenzene sulfonate-type, α-olefin sulfonate-type, and alkanesulfonic acid-type anionic surfactants; and phosphoric acid ester-based anionic surfactants, such as alkyl phosphates and alkyl ether phosphates. Among these anionic surfactants, preferred are carboxylic acid-based and sulfuric acid ester-based anionic surfactants. In particular, carboxylic acid-based anionic surfactants are preferred. Among the carboxylic acid-based anionic surfactants, preferred are N-acylamino acid salts and ether carboxylates. Particularly preferred are N-acyl glutamates of which the acyl groups have 10 to 18 carbon atoms, preferably 10 to 16 and more preferably 10 to 14 carbon atoms; and polyoxyethylene alkyl carboxylates of which the alkyl groups have 10 to 18 carbon atoms, preferably 10 to 16, and more preferably 10 to 14 carbon atoms and in which the number of average addition moles of the oxyethylene groups is from 3 to 15, preferably from 3 to 12, and more preferably from 4 to 10.

Examples of the nonionic surfactant include alkyl polyglycosides, polyoxyalkylene alkyl ethers, and alkyl glyceryl ethers. The alkyl polyglycosides are preferably those of which the alkyl groups have 8 to 18 carbon atoms, more preferably 8 to 14, and even more preferably 9 to 11 and are preferably linear, and the glycosides preferably have an average degree of polymerization of from 1 to 5 and more preferably from 1 to 2. The polyoxyalkylene alkyl ethers are preferably those of which the alkyl groups have 10 to 22 and more preferably 12 to 18 carbon atoms and are preferably linear, and are more preferably polyoxyethylene alkyl ethers, in particular, those in which the number of average addition moles of the oxyethylene groups is from 1 to 50 and more preferably from 2 to 40. The alkyl glyceryl ethers are preferably those of which the alkyl groups have 8 to 18 and more preferably 8 to 12 carbon atoms and preferably are branched.

The cationic surfactant is preferably a mono-long-chain-alkyl quaternary ammonium salt or a di-long-chain-alkyl quaternary ammonium salt, and examples thereof include cetrimonium chloride, steartrimonium chloride, behentrimonium chloride, stearalkonium chloride, benzalkonium chloride, stearoxypropyltrimonium chloride, and dialkyl (C12-18) dimonium chloride. Steartrimonium chloride, behentrimonium chloride, stearoxypropyltrimonium chloride, and dialkyl (C12-18) dimonium chloride are more preferred. Examples of commercial product of the cationic surfactant include Quartamin series 86W, 86P Conc, 60W, E-80K, and D2345P (manufactured by Kao Corporation), and Nikkol CA-2580 (manufactured by Nihon Surfactant Kogyo K.K.).

Examples of the amphoteric surfactants include carbobetaine-based, amidobetaine-based, sulfobetaine-based, hydroxysulfobetaine-based, amidosulfobetaine-based, phosphobetaine-based, and imidazolinium-based surfactants having alkyl, alkenyl, or acyl groups having 8 to 24 carbon atoms. In particular, carbobetaine-based surfactants and sulfobetaine-based surfactants are preferred. Preferred examples of the amphoteric surfactant include laurylic acid amidopropyl betaine, coconut oil fatty acid amidopropyl betaine, lauryl dimethylaminoacetic betaine, and lauryl hydroxysulfobetaine.

The surfactants may be used in combination of two or more thereof, and the content thereof in the hair cosmetic is preferably 0.1% by mass or more, more preferably 0.5% by mass or more, and even more preferably 1% by mass or more and preferably 30% by mass or less, more preferably 25% by mass or less, more preferably 20% by mass or less, and even more preferably 15% by mass or less, from the viewpoint of the stability of the hair cosmetic.

When the hair cosmetic of the present invention is a shampoo, the shampoo preferably contains an anionic surfactant, in particular, a sulfuric acid ester-based anionic surfactant, such as an alkyl sulfate or an alkyl ether sulfate, from the viewpoint of foaming and cleansing properties. The content of the anionic surfactant in the shampoo is preferably 2% by mass or more, more preferably 2.5% by mass or more, more preferably 3% by mass or more, and even more preferably 5% by mass or more and preferably 30% by mass or less, more preferably 25% by mass or less, more preferably 20% by mass or less, and even more preferably 15% by mass or less. The mass ratio of the anionic surfactant to the total mass of Component (A) and Component (B) (anionic surfactant/(Component (A)+Component (B))) is preferably 0.3 or more, more preferably 0.5 or more, more preferably 1 or more, and even more preferably 1.5 or more and preferably 10 or less, more preferably 8 or less, more preferably 7 or less, and even more preferably 4 or less, from the viewpoint of the stability of the shampoo.

When the hair cosmetic of the present invention is a hair rinse, hair conditioner, or hair treatment agent, the hair cosmetic preferably contains a cationic surfactant, in particular, a mono-long-chain-alkyl quaternary ammonium salt or a di-long-chain-alkyl quaternary ammonium salt, from the viewpoint of providing smoothness to the hair after rinsing or drying. The content of the cationic surfactant in the hair rinse, hair conditioner, or hair treatment agent is preferably 0.1% by mass or more, more preferably 0.5% by mass or more, and even more preferably 1% by mass or more and preferably 15% by mass or less, more preferably 10% by mass or less, and even more preferably 8% by mass or less. The mass ratio of the cationic surfactant to the total mass of Component (A) and Component (B) (cationic surfactant/(Component (A)+Component (B))) is preferably 0.3 or more, more preferably 0.5 or more, and even more preferably 1 or more and preferably 10 or less, more preferably 8 or less, more preferably 6 or less, more preferably 4 or less, and even more preferably 2 or less, from the viewpoint of stability of the hair rinse, hair conditioner, or hair treatment agent.

When the hair cosmetic of the present invention is a hair bleach or dye composition, the content of the surfactant is preferably 2% by mass or more, more preferably 2.5% by mass or more, and even more preferably 3% by mass or more and preferably 20% by mass or less, more preferably 15% by mass or less, more preferably 10% by mass or less, more preferably 8% by mass or less, more preferably 7% by mass or less, and even more preferably 6% by mass or less, from the viewpoint of the stability of the hair bleach or dye composition.

[Higher Alcohol]

The hair cosmetic of the present invention preferably contains a higher alcohol having 12 or more carbon atoms from the viewpoint of an improvement in feel and stability. The higher alcohol forms a structure with a surfactant to prevent separation and improves the feel during rinsing. When the hair cosmetic is of a two-part or three-part system, the higher alcohol may be contained in any of the first part, the second part, and the third part.

The higher alcohol preferably has 12 or more, more preferably 16 or more, carbon atoms and preferably 30 or less, more preferably 22 or less, carbon atoms, and examples thereof include myristyl alcohol, cetyl alcohol, stearyl alcohol, arachyl alcohol, behenyl alcohol, ostearyl alcohol, 2-octyldodecanol, and oleyl alcohol, and mixtures thereof.

The higher alcohols may be used in combination of two or more thereof, and the content thereof is preferably 3% by mass or more and more preferably 4% by mass or more and preferably 11% by mass or less and more preferably 9% by mass or less based on the total amount of the hair cosmetic, from the viewpoint of the viscosity and stability of the hair cosmetic.

[Polyol]

The hair cosmetic of the present invention preferably further contains a polyol. When the hair cosmetic is of a two-part or three-part system, the polyol may be contained in any of the first part, the second part, and the third part. Examples of the polyol include: those having 2 to 20 carbon atoms, specifically, alkylene glycols, such as ethylene glycol, diethylene glycol, triethylene glycol, polyethylene glycol, propylene glycol, dipropylene glycol, polypropylene glycol, 1,2-butylene glycol, 1,3-butylene glycol, pentylene glycol, and hexylene glycol; glycerins, such as glycerin, diglycerin, and polyglycerin; sugar alcohols, such as xylitol, mannitol, galactitol, and sorbitol; and other polyols, such as trimethylolethane, trimethylolpropane, and pentaerythritol.

The polyols may be used in combination of two or more thereof. The content of the polyol in the hair cosmetic is preferably 0.1% by mass or more, more preferably 0.5% by mass or more, and even ore preferably 1% by mass or more and preferably 20% by mass or less, more preferably 15% by mass or less, and even more preferably 10% by mass or less, in terms of excellent effects of providing moisture to the hair and preventing hair dryness.

[Conditioning Component]

The hair cosmetic of the present invention can contain a conditioning component selected from the group consisting of silicones and oils.

Examples of the silicones include polydimethylsiloxanes, modified silicones (e.g., amino-modified silicone, fluorine-modified silicone, alcohol-modified silicone, polyether-modified silicone, epoxy-modified silicone, alkyl-modified silicone, and aminopolyether-modified silicone), cyclic polydimethylsiloxanes, and highly polymerized methylpolysiloxane emulsion. In particular, polydimethylsiloxanes, polyether-modified silicones, amino-modified silicone, cyclic polydimethylsiloxane, aminopolyether-modified silicone, and highly polymerized methylpolysiloxane emulsion are preferred.

These silicones may be used alone or in combination of two or more thereof. The content of the silicones in the hair cosmetic is preferably 0.1% by mass or more and more preferably 0.5% by mass or more from the viewpoint of providing sufficient effects, and 20% by mass or less and more preferably 15% by mass or less from the viewpoint of preventing stickiness.

Examples of the oils include: hydrocarbons, such as squalene, squalane, vaseline, paraffin, liquid paraffin, liquid isoparaffin, and cycloparaffin; glycerides, such as castor oil, cacao oil, mink oil, avocado oil, olive oil, and shea fat; waxes, such as beeswax, whale wax, lanolin, and carnauba wax; ester oils, such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanate, and tridecyl isononanate; and higher fatty acids, such as capric acid, lauric acid, myristic acid, palmitic acid, stearic acid, behenic acid, oleic acid, lanolin fatty acid, iso fatty acid, anti-iso fatty acid, coconut oil fatty acid, 18-methyleicosanoic acid, 16-methyloctadecanoic acid, and mixtures of these fatty acids/branched fatty acids.

These oils may be used alone or in combination of two or more thereof. The content of the oil in the hair cosmetic is 0.1% by mass or more and more preferably 0.5% by mass or more from the viewpoint of the effect of improving the feel, and 20% by mass or less and more preferably 15% by mass or less from the viewpoint of stability to prevent the separation of the hair cosmetic.

Such a conditioning component appropriately remains on the hair and, thereby, can exhibit a sufficient conditioning effect.

[Dye]

When the hair cosmetic of the present invention is a hair dye composition, the hair cosmetic contains a dye. A one-part hair dye composition contains a direct dye. A two-part or three-part hair dye composition can contain an oxidation dye intermediate or a direct dye in the first part.

(Oxidation Dye Intermediate)

The oxidation dye intermediate can be known precursor and coupler that are usually contained in hair dyes. Examples of the precursor include para-phenylenediamine, toluene-2,5-diamine, N-phenyl para-phenylenediamine, N,N-bis(hydroxyethyl) para-phenylenediamine, 2-hydroxyethyl para-phenylenediamine, para-aminophenol, para-methylaminophenol, 4-amino-meta-cresol, and ortho-aminophenol, and salts thereof.

Examples of the coupler include resorcin, 2-methylresorcin, 1-naphthol, 1,5-dihydroxynaphthalene, 5-amino-o-cresol, m-phenylenediamine, m-aminophenol, 2,4-diaminophenoxyethanol, 2,6-diaminopyridine, 2-methyl-5-hydroxyethylaminophenol, and 2-amino-3-hydroxypyridin, and salts thereof.

The precursors may be used in combination of two or more thereof, and the couplers also may be used in combination of two or more thereof. The contents of the precursor and the coupler in the hair dye composition are each preferably 0.01% by mass or more, more preferably 0.1% by mass or more, and preferably 5% by mass or less, more preferably 4% by mass or less.

(Direct Dye)

Examples of the direct dye include acid dyes, nitro dyes, disperse dyes, and basic dyes. More specifically, examples of the acid dye include Blue No. 1, Violet No. 401, Black No. 401, Orange No. 205, Red No. 227, Red No. 106, Yellow No. 203, and Acid Orange 3; examples of the nitro dye include 2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, HC Blue 2, HC Orange 1, HC Red 1, HC Yellow 2, HC Yellow 4, HC Yellow 5, HC Red 3, and N,N-bis(2-hydroxyethyl)-2-nitro-p-phenylenediamine; examples of the disperse dye include Disperse Violet 1, Disperse Blue 1, and Disperse Black 9, and examples of the basic dye include Basic Blue 99, Basic Brown 16, Basic Brown 17, Basic Red 76, Basic Yellow 76, Basic Orange 31, and Basic Red 51.

The direct dyes may be used in combination of two or more thereof. A two-part or three-part hair dye composition may contain both the direct dye and the oxidation dye intermediate. The content of the direct dye in the hair dye composition is preferably 0.001% by mass or more, more preferably 0.01% by mass or more, and preferably 5% by mass or less, more preferably 3% by mass or less.

[Alkaline Agent]

When the hair cosmetic of the present invention is a hair bleach or dye composition, the hair cosmetic can contain an alkaline agent. In a two-part or three-part hair bleach or dye composition, the first part contains the alkaline agent. Examples of the alkaline agent include: ammonia and salts thereof; sodium hydroxide; potassium hydroxide; alkanolamines, such as monoethanolamine, isopropanolamine, 2-amino-2-methylpropanol, and 2-aminobutanol, and salts thereof; alkanediamines, such as 1,3-propanediamine, and salts thereof; and carbonates, such as sodium carbonate, potassium carbonate, sodium bicarbonate, potassium bicarbonate, and guanidine carbonate.

The alkaline agents may be used in combination of two or more thereof, and the content thereof in the hair bleach or dye composition is preferably 0.05% by mass or more, more preferably 0.1% by mass or more, and even more preferably 0.2% by mass or more, in terms of providing a sufficient hair coloring effect, and is preferably 5% by mass or less and more preferably 3% by mass or less, in terms of reducing the hair damage and scalp irritation.

[Hydrogen Peroxide]

When the hair bleach or dye composition of the present invention is of a two-part or three-part system, the second part can contain hydrogen peroxide. The content of the hydrogen peroxide in the hair bleach or dye composition is preferably 0.1% by mass or more, more preferably 0.5% by mass or more, and even more preferably 1% by mass or more, in terms of providing a sufficient hair coloring effect, and is preferably 12% by mass or less, more preferably 9% by mass or less, and even more preferably 6% by mass or less, in terms of reducing the hair damage and scalp irritation.

[Other Optional Components]

The hair cosmetic of the present invention can contain other components that are usually used as cosmetic raw materials, in addition to the above-described components. Examples of such optional components include thickeners, preservatives, chelating agents, stabilizers, antioxidants, plant extracts, galenical extracts, protein hydrolysates, vitamins, coloring agents such as dyes, fragrances, UV absorbers, pearl ingredients such as ethylene glycol difatty acid esters, hair setting polymers, and amphipathic amide lipids.

Examples of the hair setting polymer include: polysilicone-9; polyvinylpyrrolidone polymers (e.g., polyvinylpyrrolidone, vinylpyrrolidone/vinyl acetate copolymer, vinylpyrrolidone/vinyl acetate/vinyl propionate terpolymer, vinylpyrrolidone/alkyl amino acrylate (quaternary chloride) copolymer, vinylpyrrolidone/acrylate/(meth)acrylic acid copolymer, and vinylpyrrolidone/alkyl aminoacrylate/vinylcaprolactam copolymer); methyl vinyl ether/maleic anhydride alkyl half-ester copolymers; acid-poly(vinyl acetate) polymers (e.g., vinyl acetate/crotonic acid copolymer, vinyl acetate/crotonic acid/vinyl neodecanoate copolymer, and vinyl acetate/crotonic acid/vinyl propionate copolymer); acid (meth)acrylate polymers (e.g., (meth)acrylic acid/ (meth)acrylic acid ester copolymer and acrylic acid/acrylic acid alkyl ester/alkyl acrylamide copolymer); amphoteric acrylic polymers (e.g., N-methacryloyl ethyl-N,N-dimethylammonium-α-N-methylcarboxybetaine/butyl methacrylate copolymer and hydroxypropyl acrylate/butyl aminoethyl methacrylate/acrylic acid octylamide copolymer); acrylamide-acrylic acid ester copolymers; and chitin-chitosan compounds (e.g., hydroxypropyl chitosan, carboxymethyl chitin, and carboxymethyl chitosan).

The content of the hair setting polymer in the hair cosmetic is preferably 0.1% by mass or more and more preferably-0.5% by mass or more and preferably 5% by mass or less and more preferably 3% by mass or less. The hair setting polymer is more suitably contained in the hair cosmetic being a styling agent.

[Medium]

The hair cosmetic of the present invention includes water as the medium. The content of water in the hair cosmetic is preferably 10% by mass or more, more preferably 20% by mass or more, and even more preferably 30% by mass or more and preferably 90% by mass or less, more preferably 80% by mass or less, and even more preferably 75% by mass or less.

The hair cosmetic of the present invention further optionally contains an organic solvent, in addition to water. Examples of the organic solvent include: aromatic alcohols, such as benzyl alcohol and benzyloxy ethanol; lower alkanols, such as ethanol and 2-propanol; polyols, such as propylene glycol, 1,3-butanediol, diethylene glycol, and glycerin; cellosolves, such as ethyl cellosolve, butyl cellosolve, and benzyl cellosolve; and carbitols, such as ethyl carbitol and butyl carbitol.

[pH]

When the hair cosmetic of the present invention is not a hair bleach or dye composition, the pH at 25° C. of the hair cosmetic is preferably 2 or more, more preferably 4.5 or more, and even more preferably 5.5 or more and preferably 12 or less, more preferably 11.5 or less, and even more preferably 11 or less.

When the hair cosmetic of the present invention is a hair bleach or dye composition, the pH at 25° C. of the hair cosmetic is preferably as follows. When the hair bleach or dye composition is a one-part hair dye composition containing an acid dye, the pH at 25° C. is preferably 1 or more and more preferably 2.5 or more and preferably 5.5 or less and more preferably 4.5 or less. When the composition is a one-part hair dye composition containing a basic dye, the pH is 3.5 or more and more preferably 4 or more and preferably 8 or less and more preferably 6 or less. In a two-part or three-part hair bleach or dye composition, the first part preferably has a pH (25° C.) of from 8 to 12; the second part preferably has a pH (25° C.) of from 2 to 5; the mixture of the first part and second part or the mixture of the first part, second part, and third part preferably has a pH (25° C.) of from 8 to 11.5 and more preferably from 9 to 11, in terms of the effect of bleaching or dyeing and skin irritation.

In order to adjust the pH, a pH adjuster can be used. Examples of the pH adjuster being an alkaline agent include ammonia and salts thereof; alkanolamines, such as monoethanolamine, isopropanolamine, 2-amino-2-methylpropanol, and 2-aminobutanol, and salts thereof; alkanediamines, such as 1,3-propanediamine, and salts thereof; carbonates, such as guanidine carbonate, sodium carbonate, potassium carbonate, sodium bicarbonate, and potassium bicarbonate; and hydroxides, such as sodium hydroxide and potassium hydroxide. Examples of the pH adjuster being an acid agent include inorganic acids, such as hydrochloric acid and phosphoric acid; organic acids, such as citric acid, glycolic acid, and lactic acid; hydrochlorides, such as monoethanolamine hydrochloride; and phosphates, such as potassium dihydrogen phosphate and disodium hydrogen phosphate.

In the use of these pH adjusters, the acid agent may be used alone; the alkaline agent may be used alone; or a combination of the both may be used. The content of the pH adjuster in the hair cosmetic is preferably 0.01% by mass or more and more preferably 0.1% by mass or more and preferably 20% by mass or less and more preferably 15% by mass or less, from the viewpoint of reducing the hair damage and scalp irritation.

[Dosage Form]

The hair cosmetic of the present invention can be formed into, for example, a liquid, emulsion, cream, gel, paste, mousse, or aerosol dosage form. In the case of the aerosol, the content of each component and the pH of the hair cosmetic described above are those of the undiluted solution not containing propellant.

The hair cosmetic of the present invention can be suitably used in an in-bath agent, such as a pre-shampoo treatment agent, shampoo, hair rinse, hair conditioner, hair treatment agent, or after-shampoo treatment agent; an out-bath agent, such as non-aerosol foam, aerosol foam, hair gel, hair mousse, hair mist, hair lotion, hair oil, or styling agent; or a hair bleach or dye composition.

Examples of the hair bleach or dye composition include one-part hair dye compositions, two-part hair bleach or dye compositions, and three-part hair bleach or dye compositions.

The one-part hair dye composition contains a direct dye, and examples thereof include products commonly known as a hair manicure, acid color, color rinse, or color treatment agent. Examples of the product form of the one-part hair dye composition include gel, cream, and aerosol forms.

The two-part hair bleach or dye composition is composed of a first part containing an alkaline agent and a second part containing hydrogen peroxide, and examples thereof include products commonly known as a hair bleach or hair color. Examples of the product form of the two-part hair bleach or dye composition include cream, emulsion, liquid, foam, and aerosol forms.

The three-part hair bleach or dye composition is composed of the first part and the second part in the two-part hair bleach or dye composition and further a third part containing an active component (for example, a persulfate (e.g., ammonium persulfate, potassium persulfate, or sodium persulfate) for improving the bleaching strength). Examples of the product form of the three-part hair bleach or dye composition include, as in the two-part hair bleach or dye composition, cream, emulsion, liquid, foam, and aerosol forms.

[Method of Using (Hair-Treating Method)]

In the treatment of hair with the hair cosmetic of the present invention, the hair cosmetic is brought into contact with the hair directly or with a tool. The contact can be achieved by a method that is widely employed for hair cosmetics. For example, a pre-shampoo treatment agent is used by bringing an appropriate amount of the pre-shampoo treatment agent into contact with wet or dry hair before shampoo treatment, leaving them to stand for several seconds to several tens of minutes, and then rinsing the hair with running water. A shampoo is used by bringing an appropriate amount of the shampoo into contact with hair, massaging the hair for several minutes while lathering, and then rinsing the hair with running water. A hair rinse, hair conditioner, hair treatment agent, or after-shampoo treatment agent is used by bringing an appropriate amount of such a hair cosmetic into contact with hair after shampoo treatment, leaving them to stand for several seconds to several tens of minutes, and then rinsing the hair with running water. A hair mousse, hair oil, or styling agent is used by bring an appropriate amount of such a hair cosmetic into contact with hair and leaving them as is. Herein, the term "an appropriate amount" refers to an amount to give a bath ratio of the hair cosmetic to the mass of the hair of about 1:0.005 to 1:10. The treatment may be applied to the whole or part of the hair to be treated. The hair cosmetic is preferably applied to hair at a temperature of from about room temperature to body temperature. The hair cosmetic may be heated to about 50° C. for accelerating the permeation.

A hair bleach or dye composition is used by, for example, applying the hair bleach or dye composition (the mixture of the first and second parts in the two-part system or the mixture of the first to third parts in the three-part system, prepared immediately before the application) to hair, leaving them to stand for a predetermined period of time, rinsing the hair with water, and then drying the hair. The application temperature of the composition to hair is preferably from 15° C. to 45° C., and the application time is preferably from 3 to 60 minutes, more preferably from 5 to 45 minutes, and even more preferably from 10 to 30 minutes.

Regarding the embodiments described above, preferred aspects of the present invention will now be further disclosed.

<1> A hair cosmetic comprising the following components (A) and (B):

(A) a cationic polymer having a charge density of 5.0 meq/g or more and 7.0 meq/g or less; and (B) an anionic polymer comprising 80% by mass or more and 100% by mass or less of a constitutional unit represented by Formula (1) and having a weight-average molecular weight of 4,000 or more and 80,000 or less,

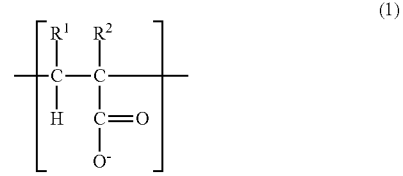

where $R^1$ represents a hydrogen atom or a carboxy group; and $R^2$ represents a hydrogen atom or a methyl group.

<2> The hair cosmetic according to aspect <1>, where Component (A) is preferably at least one selected from the group consisting of a polymer comprising a diallyl quaternary ammonium salt as a constitutional unit and a quaternized polyvinylimidazolium derivative.

<3> The hair cosmetic according to aspect <2>, where the polymer comprising a diallyl quaternary ammonium salt as a constitutional unit preferably have a skeleton represented by Formula (2) or (3):

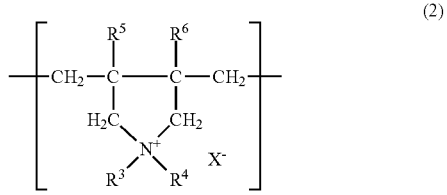

-continued

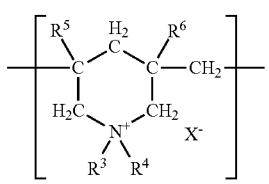

(3)

where $R^3$ and $R^4$ may be the same or different and each represent a hydrogen atom, an alkyl group having 1 to 18 carbon atoms, an aryl group (such as a phenyl group), a hydroxy alkyl group, an amido alkyl group, a cyanoalkyl group, an alkoxyalkyl group, or a carboalkoxyalkyl group; $R^5$ and $R^6$ may be the same or different and each represent a hydrogen atom, an alkyl group having 1 to 3 carbon atoms, or a phenyl group; and $X^-$ represents an anion (such as a chloride ion, a bromide ion, an iodide ion, a sulfate anion, a sulfonate anion, a methylsulfate anion, a phosphate anion, or a nitrate anion).

<4> The hair cosmetic according to aspect <3>, where each molecule of the polymer comprising a diallyl quaternary ammonium salt as a constitutional unit preferably comprises the constitutional unit represented by Formula (2) or (3) in an amount of preferably from 65% to 100 mol %, more preferably from 75% to 100 mol %, more preferably from 90% to 100 mol %, and even more preferably from 95% to 100 mol %.

<5> The hair cosmetic according to any one of aspects <2> to <4>, where the polymer comprising a diallyl quaternary ammonium salt as a constitutional unit is preferably a homopolymer of a diallyl quaternary ammonium salt or a copolymer of a diallyl quaternary ammonium salt and acrylic acid.

<6> The hair cosmetic according to aspect <2>, where the quaternized polyvinylimidazolium derivative preferably has a skeleton represented by Formula (6):

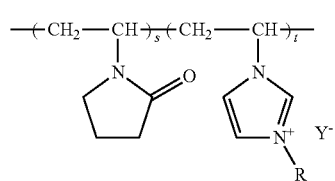

(6)

where R represents a hydrogen atom or an alkyl group having 1 to 3 carbon atoms; $Y^-$ represents an anion, such as a chloride ion, a bromide ion, an iodide ion, a sulfate anion, a sulfonate anion, an alkylsulfate anion having 1 to 4 carbon atoms, a phosphate anion, or a nitrate anion; and s and t each represent a molar ratio, provided that s+t=100.

<7> The hair cosmetic according to aspect <6>, where t in Formula (6) preferably represents 73 or more, more preferably 90 or more, and even more preferably 93 or more and preferably represents 99 or less.

<8> The hair cosmetic according to any one of aspects <1> to <7>, where Component (A) preferably has a weight-average molecular weight of 10,000 or more, more preferably 50,000 or more, and even more preferably 100,000 or more, and preferably 3,000,000 or less, more preferably 1,000,000 or less, and even more preferably 800,000 or less.

<9> The hair cosmetic according to any one of aspects <1> to <8>, where Component (A) preferably has a charge density of 5.2 meq/g or more, more preferably 5.5 meq/g or more, more preferably 5.8 meq/g or more, and even more preferably 6.0 meq/g or more, and preferably 6.5 meq/g or less.

<10> The hair cosmetic according to any one of aspects <1> to <9>, where the content of Component (A) is preferably 0.01% by mass or more, more preferably 0.1% by mass or more, more preferably 0.5% by mass or more, and even more preferably 0.75% by mass or more, and preferably 20% by mass or less, more preferably 10% by mass or less, more preferably 5% by mass or less, more preferably 3% by mass or less, more preferably 2.5% by mass or less, and even more preferably 2% by mass or less.

<11> The hair cosmetic according to any one of aspects <1> to <10>, where Component (B) comprises the constitutional unit represented by Formula (1) in an amount of preferably 85% by mass or more, more preferably 90% by mass or more, more preferably 95% by mass or more, and even more preferably 100% by mass.

<12> The hair cosmetic according to any one of aspects <1> to <11>, where Component (B) preferably has a weight-average molecular weight of 5,000 or more, more preferably 6,000 or more, more preferably 7,000 or more, and even more preferably 10,000 or more, and preferably 50,000 or less, more preferably 30,000 or less, more preferably 20,000 or less, and even more preferably 18,000 or less.

<13> The hair cosmetic according to any one of aspects <1> to <12> being a hair bleach or dye composition, where Component (B) is preferably contained in the first part when the composition is of a two-part system and is preferably contained in the first part or the third part, more preferably in the third part when the composition is of a three-part system.

<14> The hair cosmetic according to any one of aspects <1> to <13>, where the content of Component (B) is preferably 0.01% by mass or more, more preferably 0.1% by mass or more, more preferably 0.3% by mass or more, and even more preferably 0.5% by mass or more, and preferably 20% by mass or less, more preferably 10% by mass or less, more preferably 5% by mass or less, more preferably 3% by mass or less, more preferably 2% by mass or less, more preferably 1.5% by mass or less, and even more preferably 1.25% by mass or less.

<15> The hair cosmetic according to any one of aspects <1> to <14>, where the mass ratio of Component (A) to Component (B), (A)/(B), is preferably 0.1 or more, more preferably 0.5 or more, and even more preferably 1 or more, and preferably 30 or less, more preferably 15 or less, more preferably 10 or less, more preferably 5 or less, and even more preferably 3 or less.

<16> The hair cosmetic according to any one of aspects <1> to <15>, preferably further containing a surfactant selected from the group consisting of anionic surfactants, nonionic surfactants, cationic surfactants, and amphoteric surfactants.

<17> The hair cosmetic according to aspect <16>, where the content of the surfactant is preferably 0.1% by mass or more, more preferably 0.5% by mass or more, and even more preferably 1% by mass or more, and preferably 30% by mass or less, more preferably 25% by mass or less, more preferably 20% by mass or less, and even more preferably 15% by mass or less.

<18> The hair cosmetic according to any one of aspects <1> to <17>, preferably further containing a higher alcohol preferably having 12 or more carbon atoms, more preferably 16 or more, and preferably 30 or less carbon atoms, more preferably 22 or less.

<19> The hair cosmetic according to aspect <18>, where the content of the higher alcohol is preferably 3% by mass or more and more preferably 4% by mass or more and preferably 11% by mass or less and more preferably 9% by mass or less.

<20> The hair cosmetic according to any one of aspects <1> to <19>, preferably further containing a polyol having 2 to 20 carbon atoms.

<21> The hair cosmetic according to aspect <20>, where the content of the polyol is preferably 0.1% by mass or more, more preferably 0.5% by mass or more, and even more preferably 1% by mass or more, and preferably 20% by mass or less, more preferably 15% by mass or less, and even more preferably 10% by mass or less.

<22> The hair cosmetic according to any one of aspects <1> to <21>, preferably further containing a conditioning component selected from the group consisting of silicones and oils.

<23> The hair cosmetic according to aspect <22>, where the content of the silicones is preferably 0.1% by mass or more and more preferably 0.5% by mass or more and preferably 20% by mass or less and more preferably 15% by mass or less.

<24> The hair cosmetic according to aspect <22>, where the content of the oils is preferably 0.1% by mass or more and more preferably 0.5% by mass or more and preferably 20% by mass or less and more preferably 15% by mass or less.

<25> The hair cosmetic according to any one of aspects <1> to <24>, preferably further containing a hair setting polymer.

<26> The hair cosmetic according to aspect <25>, where the content of the hair setting polymer is preferably 0.1% by mass or more and more preferably 0.5% by mass or more and preferably 5% by mass or less and more preferably 3% by mass or less.

<27> The hair cosmetic according to any one of aspects <1> to <26>, being preferably selected from the group consisting of pre-shampoo treatment agents, shampoos, hair rinses, hair conditioners, hair treatment agents, after-shampoo treatment agents, non-aerosol foams, aerosol foams, hair gels, hair mousses, hair mists, hair lotions, hair oils, styling agents, and hair bleach or dye compositions.

<28> The hair cosmetic according to any one of aspects <1> to <12> and <14> to <26>, being a hair cosmetic other than hair bleach or dye compositions and preferably having a pH at 25° C. of 2 or more, more preferably 4.5 or more, and even more preferably 5.5 or more, and preferably 12 or less, more preferably 11.5 or less, and even more preferably 11 or less.

<29> The hair cosmetic according to aspect <27> or <28>, being a shampoo containing an anionic surfactant in an amount of preferably 2% by mass or more, more preferably 2.5% by mass or more, more preferably 3% by mass or more, and even more preferably 5% by mass or more, and preferably 30% by mass or less, more preferably 25% by mass or less, more preferably 20% by mass or less, and even more preferably 15% by mass or less.

<30> The hair cosmetic according to aspect <29>, where the mass ratio of the anionic surfactant to the total mass of Component (A) and Component (B) (anionic surfactant/(Component (A)+Component (B))) is preferably 0.3 or more, more preferably 0.5 or more, more preferably 1 or more, and even more preferably 1.5 or more, and preferably 10 or less, more preferably 8 or less, more preferably 7 or less, and even more preferably 4 or less.

<31> The hair cosmetic according to aspect <27> or <28>, being a hair rinse, hair conditioner, or hair treatment agent containing a cationic surfactant in an amount of preferably 0.1% by mass or more, more preferably 0.5% by mass or more, and even more preferably 1.0% by mass or more, and preferably 15% by mass or less, more preferably 10% by mass or less, and even more preferably 8% by mass or less.

<32> The hair cosmetic according to aspect <31>, where the mass ratio of the cationic surfactant to the total mass of Component (A) and Component (B) (cationic surfactant/(Component (A)+Component (B))) is preferably 0.3 or more, more preferably 0.5 or more, and even more preferably 1 or more, and preferably 10 or less, more preferably 8 or less, more preferably 6 or less, more preferably 4 or less, and even more preferably 2 or less.

<33> The hair cosmetic according to aspect <27>, being a hair bleach or dye composition containing a surfactant in an amount of preferably 2% by mass or more, more preferably 2.5% by mass or more, and even more preferably 3% by mass or more, and preferably 20% by mass or less, more preferably 15% by mass or less, more preferably 10% by mass or less, more preferably 8% by mass or less, more preferably 7% by mass or less, and even more preferably 6% by mass or less.

<34> A method of treating hair, comprising bringing the pre-shampoo treatment agent being the hair cosmetic according to aspect <27> into contact with hair in a dry state or a wet state (preferably in a dry state), leaving them to stand, then rinsing the hair with running water, and then treating the hair with a shampoo.

<35> A method of treating hair, comprising bringing an appropriate amount of the shampoo being the hair cosmetic according to aspect <27> into contact with hair, massaging the hair while lathering, and then rinsing the hair with running water.

<36> A method of treating hair, comprising bringing the hair rinse, hair conditioner, hair treatment agent, or after-shampoo treatment agent being the hair cosmetic according to aspect <27> into contact with hair after treatment with a shampoo, leaving them to stand, and then rising the hair with running water.

<37> A method of treating hair, comprising applying the hair bleach or dye composition being the hair cosmetic according to aspect <27> to hair, leaving them to stand at 15° C. to 45° C. for 3 to 60 minutes, rinsing the hair with water, and then drying the hair.

EXAMPLES

Examples 1 to 12 and Comparative Examples 1 to 6

Hair cosmetics shown in Tables 1 to 3 were prepared by common processes. The measurement of combing force and evaluation of finger combability of wet hair and manageability of dried hair were performed in accordance with the following methods and criteria.

Method of Treating Hair

Tresses (each 10 g) of Japanese hair (length: 30 cm) damaged by repeated bleaching and washing were prepared. The hair at this stage was defined as untreated hair. The hair cosmetics (pre-shampoo treatment agent compositions) shown in Tables 1 to 3 were applied to the respective hair tresses at a bath ratio (mass, of the hair:mass of aqueous solution) of 1:1, rinsing the hair with running water, and then drying the hair. The hair at this stage was defined as hair immediately after treatment. The hair was further washed with a shampoo and dried under normal conditions for 14 times. The hair at this stage was defined as hair after 14 times of shampooing.

Evaluation of Physical Properties (Combing Force Test)

In order to evaluate the physical properties, the hair tresses treated by the above-described processes (immediately after treatment and after 14 times of shampooing) were each hung from a force gauge. Each hair tress was pinched with two hairbrushes from the front and back or both sides and was combed 15 times. The force applied in each combing was measured with a measuring apparatus described in J. Soc. Cosmet. Chem. Japan., Vol. 27, No. 1, pp. 11-13, 1993. The combing rate was about one time per second. The combability was evaluated by the average of the measured combing forces (maximum values) in ten times excluding the first five times. The hairbrushes used were Kao Lunettes (total length: about 20 cm, comb portion size: about 4×10 cm, density of comb teeth: 6 teeth/cm). The averages of each ten measured values (maximum values) are shown in Tables 1 to 3.

Sensory Evaluation (Finger Combability of Wet Hair)

The hair tresses treated by the above-described processes (immediately after treatment and after shampooing) were wetted with water and sensory evaluated for the finger combability by ten expert panelists according to the following five criteria. The total scores are shown in Tables 1 to 3.

+2: Better finger combability than that in Comparative Example 1

+1: Somewhat better finger combability than that in Comparative Example 1

0: Substantially equal finger combability to that in Comparative Example 1

−1: somewhat worse finger combability than that in Comparative Example 1

−2: Worse finger combability than that in Comparative Example 1

Sensory Evaluation (Manageability of Dried Hair)

The hair tresses treated by the above-described processes (immediately after treatment and after shampooing) were sensory evaluated for the manageability (in a dry state) by ten expert panelists according to the following five criteria. The total scores are shown in Tables 1 to 3.

+2: No sticking-up hair and better manageability than that in Comparative Example 1

+1: Somewhat better manageability than that in Comparative Example 1

0: Substantially equal manageability to that in Comparative Example 1

−1: Somewhat worse manageability than that in Comparative Example 1

−2: Plenty of sticking-up hair and worse manageability than that in Comparative Example 1

TABLE 1

| | Component (% by weight; active component) | | Examples 1 | 2 | 3 | 4 | 5 | 6 | 7 |
|---|---|---|---|---|---|---|---|---|---|
| (A) | Dimethyl diallyl ammonium chloride homopolymer*[1] | | 1.33 | 1.33 | 1.33 | — | — | — | 1.33 |
| | Dimethyl diallyl ammonium chloride/acrylic acid (95:5) copolymer*[2] | | — | — | — | 1.33 | — | — | — |
| | Dimethyl diallyl ammonium chloride/acrylic acid (65:35) copolymer*[3] | | — | — | — | — | 1.33 | — | — |
| | Vinylpyrrolidone/N-methylvinylimidazolinium chloride (94:6) copolymer*[4] | | — | — | — | — | — | 1.33 | — |
| | Dimethyl diallyl ammonium chloride/acrylamide (30:70) copolymer*[5] | | — | — | — | — | — | — | — |
| (B) | Sodium polyacrylate (weight-average molecular weight: 5,000)*[6] | | 0.67 | — | — | — | — | — | — |
| | Sodium polyacrylate (weight-average molecular weight: 8,000)*[7] | | — | 0.67 | — | — | — | — | — |
| | Sodium polyacrylate (weight-average molecular weight: 15,000)*[8] | | — | — | 0.67 | 0.65 | 0.54 | 0.66 | 0.67 |
| | Sodium polyacrylate (weight-average molecular weight: 100,000)*[9] | | — | — | — | — | — | — | — |
| | Cross-linked sodium polyacrylate*[10] | | — | — | — | — | — | — | — |
| Others | Sodium chloride | | 2.0 | 2.0 | 2.0 | 2.0 | 2.0 | 2.0 | 2.0 |
| | pH adjuster | | q.s. | q.s. | q.s. | q.s. | q.s. | q.s. | q.s. |
| | Purified water | | Balance | Balance | Balance | Balance | Balance | Balance | Balance |
| | Total | | 100 | 100 | 100 | 100 | 100 | 100 | 100 |
| | pH | | 6.0 | 6.0 | 6.0 | 6.0 | 6.0 | 6.0 | 10.0 |
| | Mass ratio (A)/(B) | | 2.0 | 2.0 | 2.0 | 2.1 | 2.5 | 2.0 | 2.0 |
| Evaluation of physical properties | Combing force (g) | Immediately after treatment | 225 | 221 | 215 | 218 | 235 | 248 | 213 |
| | | After 14 times of shampooing | 380 | 361 | 338 | 345 | 365 | 378 | 335 |
| Sensory evaluation | Smoothness in finger combing (wet hair) | Immediately after treatment | 11 | 11 | 12 | 12 | 10 | 10 | 12 |
| | | After 14 times of shampooing | 9 | 9 | 11 | 10 | 7 | 7 | 11 |
| | Manageability (dry hair) | Immediately after treatment | 11 | 11 | 11 | 11 | 11 | 12 | 11 |
| | | After 14 times of shampooing | 7 | 8 | 9 | 9 | 7 | 9 | 10 |

TABLE 2

| | Component (% by weight; active component) | Examples 8 | 9 | 10 | 11 | 12 |
|---|---|---|---|---|---|---|
| (A) | Dimethyl diallyl ammonium chloride homopolymer*¹ | 0.67 | 2.00 | 2.66 | 1.33 | 1.33 |
| | Dimethyl diallyl ammonium chloride/acrylic acid (95:5) copolymer*² | — | — | — | — | — |
| | Dimethyl diallyl ammonium chloride/acrylic acid (65:35) copolymer*³ | — | — | — | — | — |
| | Vinylpyrrolidone/N-methylvinylimidazolinium chloride (94:6) copolymer*⁴ | — | — | — | — | — |
| | Dimethyl diallyl ammonium chloride/acrylamide (30:70) copolymer*⁵ | — | — | — | — | — |
| (B) | Sodium polyacrylate (weight-average molecular weight: 5,000)*⁶ | — | — | — | — | — |
| | Sodium polyacrylate (weight-average molecular weight: 8,000)*⁷ | — | — | — | — | — |
| | Sodium polyacrylate (weight-average molecular weight: 15,000)*⁸ | 0.34 | 1.01 | 1.34 | 0.54 | 0.96 |
| | Sodium polyacrylate (weight-average molecular weight: 100,000)*⁹ | — | — | — | — | — |
| | Cross-linked sodium polyacrylate*¹⁰ | — | — | — | — | — |
| Others | Sodium chloride | 2.0 | 2.0 | 2.0 | 2.0 | 2.0 |
| | pH adjuster | q.s. | q.s. | q.s. | q.s. | q.s. |
| | Purified water | Balance | Balance | Balance | Balance | Balance |
| | Total | 100 | 100 | 100 | 100 | 100 |
| | pH | 6.0 | 6.0 | 6.0 | 6.0 | 6.0 |
| | Mass ratio (A)/(B) | 2.0 | 2.0 | 2.0 | 2.5 | 1.4 |
| Evaluation of physical properties | Combing force (g) Immediately after treatment | 229 | 236 | 235 | 223 | 229 |
| | After 14 times of shampooing | 351 | 354 | 352 | 340 | 344 |
| Sensory evaluation | Smoothness in finger combing (wet hair) Immediately after treatment | 11 | 12 | 11 | 12 | 11 |
| | After 14 times of shampooing | 10 | 10 | 9 | 10 | 9 |
| | Manageability (dry hair) Immediately after treatment | 10 | 11 | 11 | 11 | 11 |
| | After 14 times of shampooing | 9 | 9 | 8 | 8 | 8 |

TABLE 3

| | Component (% by weight; active component) | Comparative Examples 1 | 2 | 3 | 4 | 5 | 6 |
|---|---|---|---|---|---|---|---|
| (A) | Dimethyl diallyl ammonium chloride homopolymer*¹ | 1.33 | 1.33 | 1.33 | — | — | — |
| | Dimethyl diallyl ammonium chloride/acrylic acid (95:5) copolymer*² | — | — | — | — | — | — |
| | Dimethyl diallyl ammonium chloride/acrylic acid (65:35) copolymer*³ | — | — | — | — | — | — |
| | Vinylpyrrolidone/N-methylvinylimidazolinium chloride (94:6) copolymer*⁴ | — | — | — | — | — | — |
| | Dimethyl diallyl ammonium chloride/acrylamide (30:70) copolymer*⁵ | — | — | — | 1.33 | 1.33 | 1.33 |
| (B) | Sodium polyacrylate (weight-average molecular weight: 5,000)*⁶ | — | — | — | — | — | — |
| | Sodium polyacrylate (weight-average molecular weight: 8,000)*⁷ | — | — | — | — | — | — |
| | Sodium polyacrylate (weight-average molecular weight: 15,000)*⁸ | — | — | — | 0.34 | — | — |
| | Sodium polyacrylate (weight-average molecular weight: 100,000)*⁹ | — | 0.67 | — | — | 0.34 | — |
| | Cross-linked sodium polyacrylate*¹⁰ | — | — | 0.67 | — | — | 0.34 |
| Others | Sodium chloride | 2.0 | 2.0 | 2.0 | 2.0 | 2.0 | 2.0 |
| | pH adjuster | q.s. | q.s. | q.s. | q.s. | q.s. | q.s. |
| | Purified water | Balance | Balance | Balance | Balance | Balance | Balance |
| | Total | 100 | 100 | 100 | 100 | 100 | 100 |
| | pH | 6.0 | 6.0 | 6.0 | 6.0 | 6.0 | 6.0 |
| | Mass ratio (A)/(B) | — | 2.0 | 2.0 | 4.0 | 3.9 | 3.9 |
| Evaluation of physical properties | Combing force (g) Immediately after treatment | 435 | 428 | 441 | 395 | 443 | 446 |
| | After 14 times of shampooing | 510 | 513 | 521 | 518 | 524 | 520 |
| Sensory evaluation | Smoothness in finger combing (wet hair) Immediately after treatment | 0 | −2 | 1 | 3 | −2 | −1 |
| | After 14 times of shampooing | 0 | 0 | 0 | 0 | 0 | 0 |
| | Manageability (dry hair) Immediately after treatment | 0 | −2 | 1 | 3 | −1 | 0 |
| | After 14 times of shampooing | 0 | 0 | 0 | 0 | 0 | 0 |

1: Merquat 100 (manufactured by Lubrizol Advanced Materials, Inc., charge density: 6.2 meq/g)
2: Merquat 295 (manufactured by Lubrizol Advanced Materials, Inc., charge density: 6.0 meq/g)
3: Merquat 280 (manufactured by Lubrizol Advanced Materials, Inc., charge density: 5.0 meq/g)
4: Luviquat Excellence (manufactured by BASF SE, charge density: 6.1 meq/g)
5: Merquat 550 (manufactured by Lubrizol Advanced Materials, Inc., charge density: 3.1 meq/g)
6: Equivalent neutralization product of Julimar AC-10S (manufactured by Toagosei Co., Ltd.)
7: Poly(acrylic acid, sodium salt) solution (manufactured by Sigma-Aldrich Corporation, Catalog No. 416029)
8: Poly(acrylic acid, sodium salt) solution (manufactured by Sigma-Aldrich Corporation, Catalog No. 416037)
9: Equivalent neutralization product of poly(acrylic acid) solution (manufactured by Sigma-Aldrich Corporation, Catalog No. 523925)

10: Carbopol 981 (manufactured by The Lubrizol Corporation)

Formulation Example 1

(Shampoo): (% by Mass)

| | |
|---|---:|
| Sodium polyacrylate aqueous solution (35% by mass)[*1]: | 4.0 |
| Dimethyl diallyl ammonium chloride/acrylic acid copolymer solution (40% by mass)[*2]: | 6.0 |
| Polyoxyethylene (2) sodium lauryl ether sulfate: | 11.0 |
| Polyoxypropylene (3) octyl ether: | 1.0 |
| Mono-2-ethylhexyl glyceryl ether: | 1.0 |
| Lauryl hydroxy sulfobetaine: | 2.0 |
| Polyoxyethylene (6) stearyl ether: | 2.0 |
| Lauric acid: | 0.8 |
| Dipotassium glycyrrhizinate: | 0.1 |
| Coconut oil fatty acid monoethanolamide: | 1.0 |
| Laurylic acid amidopropyl betaine: | 0.5 |
| Dimethylpolysiloxane[*3]: | 1.5 |
| Aminopolyether-modified silicone[*4]: | 0.2 |
| Ethylene glycol distearyl ester: | 1.5 |
| Dipropylene glycol: | 3.0 |
| Benzyloxy ethanol: | 0.5 |
| L-Menthol: | 1.0 |
| Sodium chloride: | 1.0 |
| Fragrance: | q.s. |
| pH adjuster (sodium hydroxide): | amount to give pH 5.0 |
| Purified water: | balance |
| Total: | 100 |

[*1]Poly(acrylic acid, sodium salt) solution (Sigma-Aldrich Corporation, Catalog No. 416037, weight-average molecular weight: 15,000)
[*2]Merquat 295 (manufactured by Lubrizol Advanced Materials, Inc., charge density: 6.0 meq/g)
[*3]Silicone CF2450 (Dow Corning Toray Co., Ltd.)
[*4]Silicone SILSTYLE104 (Dow Corning Toray Co., Ltd.)

Formulation Example 2

(Hair Treatment Agent): (% by Mass)

| | |
|---|---:|
| Sodium polyacrylate aqueous solution (35% by mass)[*1]: | 2.0 |
| Dimethyl diallyl ammonium chloride/acrylic acid copolymer solution (40% by mass)[*2]: | 3.13 |
| Stearic acid dimethylaminopropylamide: | 1.0 |
| Behenyl alcohol: | 4.0 |
| Stearyl alcohol: | 3.0 |
| Benzyl alcohol: | 1.0 |
| Polypropylene glycol (molecular weight: 300): | 1.0 |
| Behenyltrimethylammonium chloride: | 1.5 |
| Highly polymerized methylpolysiloxane[*3]: | 2.0 |
| Squalene: | 1.0 |
| Hydroxyethyl cellulose (molecular weight: 500,000): | 0.3 |
| Isononyl isononanate: | 1.0 |
| Dipentaerythrite fatty acid ester[*4]: | 0.3 |
| Hydrolyzed casein: | 0.1 |
| *Aloe* extract: | 0.1 |
| Methyl paraben: | 0.1 |
| Rice germ oil: | 0.6 |
| L-Glutamic acid: | 0.5 |
| Fragrance: | 0.4 |
| Purified water: | balance |
| Total: | 100 |

[*1]Poly(acrylic acid, sodium salt) solution (Sigma-Aldrich Corporation, Catalog No. 416037, weight-average molecular weight: 15,000)
[*2]Merquat 295 (manufactured by Lubrizol Advanced Materials, Inc., charge density: 6.0 meq/g)
[*3]BY11-003 (Dow Corning Toray Co., Ltd.)
[*4]Cosmol 168M (The Nisshin Oillio Group, Ltd.)

Formulation Example 3

(Hair Gel): (% by Mass)

| | |
|---|---:|
| Sodium polyacrylate aqueous solution (35% by mass)[*1]: | 4.0 |
| Dimethyl diallyl ammonium chloride/acrylic acid copolymer solution (40% by mass)[*2]: | 6.0 |
| Ethanol: | 10.0 |
| Glycerin: | 2.0 |
| Dipropylene glycol: | 2.0 |
| Benzyl alcohol: | 0.5 |
| PEG-60 hydrogenated castor oil: | 0.3 |
| (C12-14) s-pareth-9: | 1.0 |
| Stearyl trimethyl ammonium chloride: | 0.25 |
| Hydroxyethyl cellulose: | 2.0 |
| Diethylamino hydroxybenzoyl hexyl benzoate[*3]: | 0.01 |
| Sodium chloride: | 1.0 |
| Fragrance: | 0.05 |
| pH adjuster (potassium hydroxide): | amount to give pH 5.0 |
| Purified water: | balance |
| Total: | 100 |

[*1]Poly(acrylic acid, sodium salt) solution (Sigma-Aldrich Corporation, Catalog No. 416037, weight-average molecular weight: 15,000)
[*2]Merquat 295 (manufactured by Lubrizol Advanced Materials, Inc., charge density: 6.0 meq/g)
[*3]Uvinul A PLUS (BASF SE)

Formulation Example 4

(Aerosol Foam): (% by Mass)

<Undiluted Solution>

| | |
|---|---:|
| Sodium polyacrylate aqueous solution (35% by mass)[*1]: | 2.0 |
| Dimethyl diallyl ammonium chloride/acrylic acid copolymer solution (40% by mass)[*2]: | 3.13 |
| Ethanol: | 4.5 |
| Glycerin: | 1.0 |
| Dipropylene glycol: | 2.0 |
| Benzyl alcohol: | 0.2 |
| (C12-14) s-pareth-9: | 1.0 |
| Polyoxyethylene lauryl ether (16 E.O.): | 1.0 |
| Stearyl trimethyl ammonium chloride: | 0.25 |
| Diethylamino hydroxybenzoyl hexyl benzoate[*3]: | 0.01 |
| Fragrance: | 0.05 |
| pH adjuster (potassium hydroxide): | amount to give pH 5.0 |
| Purified water: | balance |
| Total: | 100 |

[*1]Poly(acrylic acid, sodium salt) solution (Sigma-Aldrich Corporation, Catalog No. 416037, weight-average molecular weight: 15,000)
[*2]Merquat 295 (manufactured by Lubrizol Advanced Materials, Inc., charge density: 6.0 meq/g)
[*3]Uvinul A PLUS (BASF SE)

<Propellant>
  LPG (0.44 MPa)
<Undiluted Solution/Propellant Ratio>
  93.0/7.0

Formulation Example 5

(Non-Aerosol Foam): (% by Mass)

| | |
|---|---:|
| Sodium polyacrylate aqueous solution (35% by mass)[*1]: | 1.43 |
| Dimethyl diallyl ammonium chloride/acrylic acid copolymer solution (40% by mass)[*2]: | 2.5 |

-continued

| | |
|---|---|
| Ethanol: | 11.0 |
| Dipropylene glycol: | 2.0 |
| Benzyl alcohol: | 0.2 |
| Polysilicone-9: | 2.0 |
| PEG-32: | 1.0 |
| PEG-400: | 1.0 |
| (C12-14) s-pareth-9: | 1.0 |
| Stearyl trimethyl ammonium chloride: | 0.25 |
| PEG-60 hydrogenated castor oil: | 0.3 |
| PPG-10 sorbitol: | 1.0 |
| Ceteth-20: | 0.5 |
| Diethylamino hydroxybenzoyl hexyl benzoate[*3]: | 0.01 |
| Fragrance: | 0.05 |
| pH adjuster (potassium hydroxide): | amount to give pH 5.0 |
| Purified water: | balance |
| Total: | 100 |

[*1]Poly(acrylic acid, sodium salt) solution (Sigma-Aldrich Corporation, Catalog No. 416037, weight-average molecular weight: 15,000)
[*2]Merquat 295 (manufactured by Lubrizol Advanced Materials, Inc., charge density: 6.0 meq/g)
[*3]Uvinul A PLUS (BASF SE)

Examples 13 to 24 and Comparative Examples 7 to 12

The first parts (pH (25° C.) 10.2) shown in Table 4, the second part (common to all) (pH (25° C.) 3.4) shown in Table 5, and the third parts (pH (25° C.): 5.7) shown in Table 6 were prepared by common processes (the pH (25° C.) of each mixture of the first part, the second part, and the third part was 10.5). The finger combability during rinsing (immediately after hair dyeing and after the elapse of a certain time from hair dyeing) and gloss feel of dried hair (immediately after hair dyeing and after the elapse of a certain time from hair dyeing) were evaluated by ten panelists in accordance with the following methods and criteria. The total scores are shown in Tables 7 to 9.

The combing forces during rinsing (immediately after hair dyeing and after the elapse of a certain time from hair dyeing) were also measured. The results are shown in Tables 7 to 9.

<Finger Combability During Rinsing (Immediately After Hair Dyeing)>

A mixture prepared by sufficiently mixing a first part (5 g), a second part (5 g), and a third part (1 g) was applied to Japanese hair (10 g) received cosmetic treatment, such as bleaching, and the hair was left to stand for 30 minutes. The hair was then rinsed with running water, washed with a shampoo, and rinsed with running water. The finger combability during rinsing after the washing with a shampoo was sensory evaluated according to the following five criteria using that in Comparative Example 7 as a reference.

+2: Better finger combability than that in Comparative Example 7
+1: Somewhat better finger combability than that in Comparative Example 7
0: Substantially equal finger combability to that in Comparative Example 7
−1: Somewhat worse finger combability to that in Comparative Example 7
−2: Worse finger combability than that in Comparative Example 7

<Gloss Feel of Dried Hair (Immediately After Hair Dyeing)>

A mixture prepared by sufficiently mixing a first part (5 g), a second part (5 g), and a third part (1 g) was applied to Japanese hair (10 g) received cosmetic treatment, such as bleaching, and the hair was left to stand for 30 minutes. The hair was then rinsed with running water, washed with a shampoo, rinsed with running water, treated with a conditioner, rinsed with running water, and then dried. The gloss feel of the dried hair was sensory evaluated according to the following five criteria using that in Comparative Example 7 as a reference.

+2: Higher gloss than that in Comparative Example 7
+1: Somewhat higher gloss than that in Comparative Example 7
0: Substantially equal gloss to that in Comparative Example 7
−1: Somewhat less gloss to that in Comparative Example 7
−2: Less gloss than that in Comparative Example 7

<Finger Combability During Rinsing (After the Elapse of a Certain Time from Hair Dyeing)>

A mixture prepared by sufficiently mixing a first part (5 g), a second part (5 g), and a third part (1 g) was applied to Japanese hair (10 g) received cosmetic treatment, such as bleaching, and the hair was left to stand for 30 minutes. The hair was then rinsed with running water, washed with a shampoo, rinsed with running water, treated with a conditioner, rinsed with running water, and then dried. Subsequently, the procedure of rinsing with running water, washing with a shampoo, rinsing with running water, treating with a conditioner, and rinsing and drying was repeated 14 times. The finger combability during the 15th rinsing with running water was sensory evaluated according to the following five criteria using that in Comparative Example 7 as a reference.

+2: Better finger combability than that in Comparative Example 7
+1: Somewhat better finger combability than that in Comparative Example 7
0: Substantially equal finger combability to that in Comparative Example 7
−1: Somewhat worse finger combability to that in Comparative Example 7
−2: Worse finger combability than that in Comparative Example 7

<Gloss Feel of Dried Hair (After the Elapse of a Certain Time from Hair Dyeing)>

A mixture prepared by sufficiently mixing a first part (5 g), a second part (5 g), and a third part (1 g) was applied to Japanese hair (10 g) received cosmetic treatment, such as bleaching, and the hair was left to stand for 30 minutes. The hair was then rinsed with running water, washed with a shampoo, rinsed with running water, treated with a conditioner, rinsed with running water, and then dried. Subsequently, the procedure of rinsing with running water, washing with a shampoo, treating with a conditioner, and rinsing and drying was repeated 14 times. The gloss feel of the dried hair was sensory evaluated according to the following five criteria using that in Comparative Example 7 as a reference.

+2: Higher gloss than that in Comparative Example 7
+1: Somewhat higher gloss than that in Comparative Example 7
0: Substantially equal gloss to that in Comparative Example 7
−1: Somewhat less gloss to that in Comparative Example 7
−2: Less gloss than that in Comparative Example 7

<Combing Force During Rinsing (Immediately After Hair Dyeing)>

A mixture prepared by sufficiently mixing a first part (5 g), a second part (5 g), and a third part (1 g) was applied to Japanese hair (10 g) received cosmetic treatment, such as bleaching, and the hair was left to stand for 30 minutes. The hair was then rinsed with running water, washed with a shampoo, and then rinsed with running water. In order to evaluate the combing force during the rinsing after the washing with a shampoo, the treated hair was hung from a force gauge, and the hair tress was then pinched with two hairbrushes from the front and back or both sides and was combed 30 times. The force applied in each combing was measured with a measuring apparatus described in J. Soc. Cosmet. Chem. Japan., Vol. 27, No. 1, pp. 11-13, 1993. The combing rate was about one time per second. The combing force was evaluated by the average of the measured combing forces in 25 times excluding the first five times. The hairbrushes used were Kao Lunettes (total length: about 20 cm, comb portion size: about 4×10 cm, density of comb teeth: 6 teeth/cm).

<Combing Force During Rinsing (After the Elapse of a Certain Time from Hair Dyeing)>

A mixture prepared by sufficiently mixing a first part (5 g), a second part (5 g), and a third part (1 g) was applied to Japanese hair (10 g) received cosmetic treatment, such as bleaching, and the hair was left to stand for 30 minutes. The hair was then rinsed with running water, washed with a shampoo, and then rinsed with running water, and dried. This procedure was repeated, and the combing force during rinsing after the 15th washing with a shampoo was measured as in the combing force during rinsing (immediately after hair dyeing) described above.

TABLE 4

| First part | (% by mass) |
| --- | --- |
| Cationic polymer (Tables 7 to 9) | Tables 7 to 9 |
| Toluene-2,5-diamine solution (20% by mass) | 2.5 |
| Resorcin | 0.4 |
| p-Aminophenol | 0.1 |
| m-Aminophenol | 0.2 |
| 2-Methyl-5-aminophenol | 0.1 |
| Polyethylene glycol | 4.0 |
| 18-Methyleicosanoic acid | 2.0 |
| Dialkyl (12-18) dimethyl ammonium chloride solution (75% by mass, Quartamin D2345P, Kao Corporation) | 0.2 |
| Octadecylpropyl-N,N-trimethylammonium chloride | 5.5 |
| Polyoxyethylene (2) cetyl ether | 0.8 |
| Polyoxyethylene (40) cetyl ether | 2.2 |
| Stearyl alcohol | 6.0 |
| Behenyl alcohol | 1.6 |
| Dimethicone/(aminoethyl aminopropyl methicone/dimethicone) copolymer mixture (Silicone CF1046, Dow Corning Toray Co., Ltd.) | 1.5 |
| Liquid paraffin | 2.0 |
| Anhydrous sodium sulfite | 0.4 |
| Ascorbic acid | 0.4 |
| Tetrasodium edetate dihydrate | 0.1 |
| Monoethanolamine | 1.0 |
| Strong ammonia solution (28% by mass) | 7.5 |
| Guanidine carbonate | 5.0 |
| Fragrance | 0.7 |
| Purified water | Balance |
| Total | 100 |

TABLE 5

| Second part | (% by mass) |
| --- | --- |
| Aqueous hydrogen peroxide solution (35% by mass) | 16.3 |
| Polyoxyethylene (40) cetyl ether | 2.0 |
| Polyoxyethylene (2) cetyl ether | 1.8 |
| Behenyl alcohol | 4.3 |
| Stearyl alcohol | 1.8 |
| Liquid paraffin | 10.0 |
| Concentrated glycerin | 3.0 |
| Trimethyl glycine | 1.0 |
| Oxyquinoline sulfate | 0.05 |
| Hydroxyethane diphosphonate | 0.08 |
| Purified water | Balance |
| Total | 100 |

TABLE 6

| Third part | (% by mass) |
| --- | --- |
| Sodium polyacrylate (Tables 7 to 9) | Tables 7 to 9 |
| Purified water | Balance |
| Total | 100 |

TABLE 7

| | | | Examples | | | | | |
| --- | --- | --- | --- | --- | --- | --- | --- | --- |
| | | | 13 | 14 | 15 | 16 | 17 | 18 |
| | | The content of each polymer is the content in first or third part (active component) | | | | | | |
| (A) | First part | Dimethyl diallyl ammonium chloride homopolymer*1 | 3.0 | 3.0 | 3.0 | 1.5 | 4.5 | 3.0 |
| (A) | (% by mass) | Dimethyl diallyl ammonium chloride/acrylic acid (95:5) copolymer*2 | — | — | — | — | — | — |
| (A) | | Dimethyl diallyl ammonium chloride/acrylic acid (65:35) copolymer*3 | — | — | — | — | — | — |
| (A) | | Vinylpyrrolidone/N-methylvinylimidazolinium chloride (94:6) copolymer*4 | — | — | — | — | — | — |
| (A') | | Dimethyl diallyl ammonium chloride/acrylamide (30:70) copolymer*5 | — | — | — | — | — | — |
| (B) | Third part | Sodium polyacrylate (weight-average molecular weight: 5,000)*6 | 7.2 | — | — | — | — | — |
| (B) | (% by mass) | Sodium polyacrylate (weight-average molecular weight: 8,000)*7 | — | 7.2 | — | — | — | — |
| (B) | | Sodium polyacrylate (weight-average molecular weight: 15,000)*8 | — | — | 7.2 | 3.6 | 10.8 | 5.8 |
| (B') | | Sodium polyacrylate (weight-average molecular weight: 100,000)*9 | — | — | — | — | — | — |
| (B') | | Cross-linked sodium polyacrylate*10 | — | — | — | — | — | — |

TABLE 7-continued

|  |  | Examples | | | | | |
|---|---|---|---|---|---|---|---|
|  |  | 13 | 14 | 15 | 16 | 17 | 18 |
| Contents of Component (A) and Component (B) in hair dye composition after mixing (active component) | | | | | | | |
|  | Component (A) (% by mass) | 1.36 | 1.36 | 1.36 | 0.68 | 2.05 | 1.36 |
|  | Component (B) (% by mass) | 0.65 | 0.65 | 0.65 | 0.33 | 0.98 | 0.53 |
|  | Mass ratio (A)/(B) | 2.08 | 2.08 | 2.08 | 2.08 | 2.08 | 2.59 |
| Evaluation | Finger combing smoothness during rinsing (immediately after hair dyeing) | 12 | 12 | 13 | 13 | 12 | 12 |
|  | Finger combing smoothness during rinsing (after the elapse of a certain time from hair dyeing) | 11 | 11 | 12 | 11 | 13 | 11 |
|  | Gloss feel of dried hair (immediately after hair dyeing) | 11 | 11 | 12 | 11 | 11 | 11 |
|  | Gloss feel of dried hair (after the elapse of a certain time from hair dyeing) | 10 | 10 | 11 | 10 | 11 | 10 |
|  | Combing force (g) during rinsing (immediately after hair dyeing) | 312 | 301 | 298 | 295 | 298 | 302 |
|  | Combing force (g) during rinsing (after the elapse of a certain time from hair dyeing) | 350 | 345 | 332 | 340 | 320 | 341 |

TABLE 8

|  |  |  | Examples | | | | | |
|---|---|---|---|---|---|---|---|---|
|  |  |  | 19 | 20 | 21 | 22 | 23 | 24 |
| The content of each polymer is the content in first or third part (active component) | | | | | | | | |
| (A) | First part | Dimethyl diallyl ammonium chloride homopolymer*1 | 3.0 | — | — | — | 6.0 | 7.5 |
| (A) | (% by mass) | Dimethyl diallyl ammonium chloride/acrylic acid (95:5) copolymer*2 | — | 3.0 | — | — | — | — |
| (A) |  | Dimethyl diallyl ammonium chloride/acrylic acid (65:35) copolymer*3 | — | — | 3.0 | — | — | — |
| (A) |  | Vinylpyrrolidone/N-methylvinylimidazolinium chloride (94:6) copolymer*4 | — | — | — | 3.0 | — | — |
| (A') |  | Dimethyl diallyl ammonium chloride/acrylamide (30:70) copolymer*5 | — | — | — | — | — | — |
| (B) | Third part | Sodium polyacrylate (weight-average molecular weight: 5,000)*6 | — | — | — | — | — | — |
| (B) | (% by mass) | Sodium polyacrylate (weight-average molecular weight: 8,000)*7 | — | — | — | — | — | — |
| (B) |  | Sodium polyacrylate (weight-average molecular weight: 15,000)*8 | 8.8 | 6.9 | 5.8 | 71 | 14.3 | 18.2 |
| (B') |  | Sodium polyacrylate (weight-average molecular weight: 100,000)*9 | — | — | — | — | — | — |
| (B') |  | Cross-linked sodium polyacrylate*10 | — | — | — | — | — | — |
| Contents of Component (A) and Component (B) in hair dye composition after mixing (active component) | | | | | | | | |
|  | Component (A) in hair dye composition (% by mass) | | 1.36 | 1.36 | 1.36 | 1.36 | 2.72 | 3.40 |
|  | Component (B) in hair dye composition (% by mass) | | 0.80 | 0.63 | 0.53 | 0.65 | 130 | 1.65 |
|  | Mass ratio (A)/(B) | | 1.70 | 2.17 | 2.59 | 2.11 | 2.10 | 2.06 |
| Evaluation | Finger combing smoothness during rinsing (immediately after hair dyeing) | | 12 | 13 | 12 | 11 | 10 | 8 |
|  | Finger combing smoothness during rinsing (after the elapse of a certain time from hair dyeing) | | 11 | 12 | 10 | 10 | 9 | 7 |
|  | Gloss feel of dried hair (immediately after hair dyeing) | | 11 | 12 | 10 | 10 | 11 | 9 |
|  | Gloss feel of dried hair (after the elapse of a certain time from hair dyeing) | | 10 | 11 | 9 | 9 | 9 | 7 |
|  | Combing force (g) during rinsing (immediately after hair dyeing) | | 304 | 299 | 310 | 330 | 310 | 345 |
|  | Combing force (g) during rinsing (after the elapse of a certain time from hair dyeing) | | 345 | 334 | 370 | 375 | 345 | 350 |

TABLE 9

|  |  |  | Comparative Examples | | | | | |
|---|---|---|---|---|---|---|---|---|
|  |  |  | 7 | 8 | 9 | 10 | 11 | 12 |
| The content of each polymer is the content in first or third part (active component) | | | | | | | | |
| (A) | First part | Dimethyl diallyl ammonium chloride homopolymer*1 | 3.0 | 3.0 | 3.0 | — | — | — |
| (A) | (% by mass) | Dimethyl diallyl ammonium chloride/acrylic acid (95:5) copolymer*2 | — | — | — | — | — | — |
| (A) |  | Dimethyl diallyl ammonium chloride/acrylic acid (65:35) copolymer*3 | — | — | — | — | — | — |

TABLE 9-continued

| | | | Comparative Examples | | | | | |
|---|---|---|---|---|---|---|---|---|
| | | | 7 | 8 | 9 | 10 | 11 | 12 |
| (A) | | Vinylpyrrolidone/N-methylvinylimidazolinium chloride (94:6) copolymer*4 | — | — | — | — | — | — |
| (A') | | Dimethyl diallyl ammonium chloride/acrylamide (30:70) copolymer*5 | — | — | — | 3.0 | 3.0 | 3.0 |
| (B) | Third part | Sodium polyacrylate (weight-average molecular weight: 5,000)*6 | — | — | — | — | — | — |
| (B) | (% by mass) | Sodium polyacrylate (weight-average molecular weight: 8,000)*7 | — | — | — | — | — | — |
| (B) | | Sodium polyacrylate (weight-average molecular weight: 15,000)*8 | — | — | — | 3.6 | — | — |
| (B) | | Sodium polyacrylate (weight-average molecular weight: 100,000)*9 | — | 7.2 | — | — | 3.6 | — |
| (B') | | Cross-linked sodium polyacrylate*10 | — | — | 7.2 | — | — | 3.6 |
| | | Contents of Component (A) and Component (B) in hair dye composition after mixing (active component) | | | | | | |
| | | Component (A) or (A') in hair dye composition (% by mass) | 1.36 | 1.36 | 1.36 | 136 | 1.36 | 1.36 |
| | | Component (B) or (B') in hair dye composition (% by mass) | — | 0.65 | 0.65 | 0.33 | 0.33 | 0.33 |
| | | Mass ratio [(A) or (A')]/[(B) or (B')] | — | 2.08 | 2.08 | 4.17 | 4.17 | 4.17 |
| Evaluation | | Finger combing smoothness during rinsing (immediately after hair dyeing) | 0 | 2 | −2 | 2 | −2 | −4 |
| | | Finger combing smoothness during rinsing (after the elapse of a certain time from hair dyeing) | 0 | 0 | 0 | 0 | 0 | 0 |
| | | Gloss feel of dried hair (immediately after hair dyeing) | 0 | 0 | 0 | 1 | 0 | −2 |
| | | Gloss feel of dried hair (after the elapse of a certain time from hair dyeing) | 0 | 0 | 0 | 0 | 0 | 0 |
| | | Combing force (g) during rinsing (immediately after hair dyeing) | 404 | 395 | 406 | 392 | 406 | 418 |
| | | Combing force (g) during rinsing (after the elapse of a certain time from hair dyeing) | 440 | 440 | 440 | 440 | 440 | 440 |

1: Merquat 100 (manufactured by Lubrizol Advanced Materials, Inc., charge density: 6.2 meq/g)
2: Merquat 295 (manufactured by Lubrizol Advanced Materials, Inc., charge density; 6.0 meq/g)
3: Merquat 280 (manufactured by Lubrizol Advanced Materials, Inc., charge density: 5.0 meq/g)
4: Luviquat Excellence (manufactured by BASF SE, charge density: 6.1 meq/g)
5: Merquat 550 (manufactured by Lubrizol Advanced Materials, Inc., charge density: 3.1 meq/g)
6: Equivalent neutralization product of Julimar AC-10S (manufactured by Toagosei Co., Ltd.)
7: Poly(acrylic acid, sodium salt) solution (Sigma-Aldrich Corporation, Catalog No. 416029)
8: Poly(acrylic acid, sodium salt) solution (Sigma-Aldrich Corporation, Catalog No. 416037)
9: Equivalent neutralization product of poly(acrylic acid) solution (Sigma-Aldrich Corporation, Catalog No. 523925)
10: Carbopol 981 (manufactured by The Lubrizol Corporation)

Formulation Example 6

Two-Part Hair Dye Having a Mass Ratio of the First Part to the Second Part of 1:1

First Part (Cream Form): (% by Mass)

| | |
|---|---|
| Strong ammonia solution (28% by mass): | 1.5 |
| Monoethanolamine: | 3.0 |
| Ammonium bicarbonate: | 0.5 |
| Dimethyl diallyl ammonium chloride/acrylic acid copolymer solution (40% by mass)*1: | 6.8 |
| Amodimethicone (40% by mass emulsion)*2: | 1.0 |
| Highly polymerized dimethylpolysiloxane (number-average degree of polymerization: 2,700): | 1.5 |
| Dimethylpolysiloxane (number-average degree of polymerization: 550): | 4.0 |
| Cetostearyl alcohol: | 7.0 |
| Octyl dodecanol: | 1.0 |
| Polyoxyethylene (40) cetyl ether: | 2.0 |
| Polyoxyethylene (2) cetyl ether: | 1.0 |
| Stearyl trimethyl ammonium chloride solution (28% by mass): | 3.0 |
| Dialkyl (12-18) dimethyl ammonium chloride solution (75% by mass): | 0.5 |
| Propylene glycol: | 3.0 |
| Tetrasodium edetate: | 0.1 |
| Ascorbic acid: | 0.3 |
| Sodium sulfite: | 0.5 |
| Para-Phenylenediamine: | 0.4 |
| Toluene-2,5-diamine: | 0.4 |
| Para-Aminophenol: | 0.5 |
| Meta-Aminophenol: | 0.2 |
| 2-Methyl-5-aminophenol: | 0.1 |
| Resorcin: | 0.4 |
| Fragrance: | 0.5 |
| Purified water: | balance |
| Total: | 100 |

*1Merquat 295 (Lubrizol Advanced Materials, Inc., charge density: 6.0 meq/g)
*2Silicone SM8704C (Dow Corning Toray Silicone Co., Ltd.)

Second Part (Cream Form): (% by Mass)

| | |
|---|---|
| Hydrogen peroxide solution (35% by mass): | 16.2 |
| 8-Quinolinol sulfate: | 0.04 |
| Polyoxyethylene (40) cetyl ether: | 1.0 |
| Polyoxyethylene (2) cetyl ether: | 1.0 |
| Sodium polyacrylate aqueous solution (35% by mass)*3: | 3.6 |
| Cetostearyl alcohol: | 3.5 |
| Phosphoric acid: | amount to give pH 3.5 |
| Purified water: | balance |
| Total: | 100 |

*3Poly(acrylic acid, sodium salt) solution (Sigma-Aldrich Corporation, Catalog No. 416037, weight-average molecular weight: 15,000)

Formulation Example 7

Two-Part Hair Dye Having a Mass Ratio of the First Part to the Second Part of 1:1, Gel Form After Mixing First Part (Gel Form): (% by Mass)

| | |
|---|---|
| Strong ammonia solution (28% by mass): | 5.0 |
| Poly(dimethylmethylene piperidinium) solution (40% by mass)*1: | 6.8 |
| Oleic acid: | 5.0 |
| Octyldodecanol: | 1.0 |
| Polyoxyethylene (10) nonylphenyl ether: | 20.0 |
| Polyethylene glycol: | 20.0 |
| Sodium sulfite: | 0.5 |
| Para-Phenylenediamine: | 2.0 |
| Ortho-Aminophenol: | 0.5 |
| Resorcin: | 0.5 |
| Fragrance: | 0.1 |
| Purified water: | balance |
| Total: | 100 |

*1Merquat 100 (Lubrizol Advanced Materials, Inc., charge density: 6.2 meq/g)

Second Part (Liquid Form): (% by Mass)

| | |
|---|---|
| Hydrogen peroxide solution (35% by mass): | 15.0 |
| Tetrasodium edetate: | 0.5 |
| Cetanol: | 2.0 |
| Sodium lauryl sulfate: | 0.5 |
| Sodium polyacrylate aqueous solution (35% by mass)*2: | 3.6 |
| Phenacetin: | 0.1 |
| Purified water: | balance |
| Total: | 100 |

*2Poly(acrylic acid, sodium salt) solution (Sigma-Aldrich Corporation, Catalog No. 416037, weight-average molecular weight: 15,000)

Formulation Example 8

(Acid Hair Dye): (% by Mass)

| | |
|---|---|
| Black No. 401: | 0.2 |
| Violet No. 401: | 0.3 |
| Yellow No. 4: | 0.3 |
| Benzyl alcohol: | 4.0 |
| Citric acid: | 0.3 |
| Dimethyl diallyl ammonium chloride/acrylic acid copolymer solution (40% by mass)*1: | 3.4 |
| Sodium polyacrylate aqueous solution (35% by mass)*2: | 1.8 |
| Sodium N-stearoyl-N-methyltaurate: | 20.0 |
| Stearyl alcohol: | 8.0 |
| Dimethylpolysiloxane (6 cs): | 2.0 |
| Dimethylpolysiloxane emulsion polymer: | 2.0 |
| Fragrance: | 0.1 |
| Purified water: | balance |
| Total: | 100 |

*1Merquat 295 (Lubrizol Advanced Materials, Inc., charge density: 6.0 meq/g)
*2Poly(acrylic acid, sodium salt) solution (Sigma-Aldrich Corporation, Catalog No. 416037, weight-average molecular weight: 15,000)

Formulation Example 9

(Acid Dye-Containing Color Rinse): (% by Mass)

| | |
|---|---|
| Black No. 401: | 0.03 |
| Violet No. 401: | 0.01 |
| Yellow No. 4: | 0.01 |
| Benzyl alcohol: | 3.0 |
| Dipropylene glycol: | 15.0 |
| Citric acid: | 1.5 |
| Poly(dimethylmethylene piperidinium) solution (40% by mass)*1: | 3.4 |
| Sodium polyacrylate aqueous solution (35% by mass)*2: | 1.8 |
| Methylphenylpolysiloxane: | 4.0 |
| Polyoxyethylene hydrogenated castor oil EO40: | 1.0 |
| Hydroxyethyl cellulose: | 2.5 |
| Purified water: | balance |
| Total: | 100 |

*1Merquat 100 (Lubrizol Advanced Materials, Inc., charge density: 6.2 meq/g)
*2Poly(acrylic acid, sodium salt) solution (Sigma-Aldrich Corporation, Catalog No. 416037, weight-average molecular weight: 15,000)

Formulation Example 10

(Basic Dye-Containing Color Rinse): (% by Mass)

| | |
|---|---|
| Cetyltrimethylammonium chloride: | 1.00 |
| Cetostearyl alcohol: | 2.75 |
| Coconut monoethanolamide: | 1.00 |
| Paraffin wax: | 1.00 |
| Basic Blue 99: | 0.15 |
| Dimethyl diallyl ammonium chloride/acrylic acid copolymer solution (40% by mass)*1: | 3.4 |
| Sodium polyacrylate aqueous solution (35% by mass)*2: | 1.8 |
| Basic Brown 16: | 0.03 |
| HC Blue 2: | 0.15 |
| Disperse Violet 4: | 0.20 |
| Fragrance: | 0.70 |
| Preservative: | 0.25 |
| pH adjuster: | q.s. |
| Purified water: | balance |
| Total: | 100 |

*1Merquat 100 (Lubrizol Advanced Materials, Inc., charge density: 6.2 meq/g)
*2Poly(acrylic acid, sodium salt) solution (Sigma-Aldrich Corporation, Catalog No. 416037, weight-average molecular weight: 15,000)

The invention claimed is:

1. A hair cosmetic, wherein the hair cosmetic is a three-part hair dye or bleach composition comprising dimethyl diallyl ammonium chloride homopolymer having a charge density of 5.0 meq/g or more and 7.0 meq/g or less in a first part, hydrogen peroxide in a second part, and sodium polyacrylate having a weight-average molecular weight of 4,000 to 20,000 in a third part.

2. The hair cosmetic according to claim 1, wherein a content of dimethyl diallyl ammonium chloride homopolymer is 0.01% by mass and 20% by mass.

3. The hair cosmetic according to claim 1, wherein a content of sodium polyacrylate is 0.01% by mass and 20% by mass.

4. The hair cosmetic according to claim 1, wherein a mass ratio of dimethyl diallyl ammonium chloride homopolymer to sodium polyacrylate is 0.1 or more and 30 or less.

5. The hair cosmetic according to claim 1, wherein dimethyl diallyl ammonium chloride homopolymer has a charge density of 5.5 meq/g or more and 6.5 meq/g or less.

6. The hair cosmetic according to claim 1, wherein sodium polyacrylate has a weight-average molecular weight of 7,000 or more and 18,000 or less.

7. The hair cosmetic according to claim 1, wherein dimethyl diallyl ammonium chloride homopolymer has a weight-average molecular weight of 10,000 or more and 3,000,000 or less.

8. The hair cosmetic according to claim 1, further comprising a surfactant selected from the group consisting of an anionic surfactant, a nonionic surfactant, a cationic surfactant, and an amphoteric surfactant.

9. The hair cosmetic according to claim 1, further comprising a higher alcohol having 12 or more and 30 or less of carbon atoms.

10. The hair cosmetic according to claim 1, further comprising a polyol having 2 to 20 carbon atoms.

11. A method of dyeing hair or bleaching hair, comprising applying the hair cosmetic according to claim 1, leaving the hair cosmetic on hair to stand at 15° C. to 45° C. for 3 to 60 minutes, rinsing the hair with water, and then drying the hair.

* * * * *